US010555919B2

(12) United States Patent
Farez et al.

(10) Patent No.: US 10,555,919 B2
(45) Date of Patent: Feb. 11, 2020

(54) MELATONIN IN AUTOIMMUNE DISEASE

(71) Applicant: The Brigham and Women's Hopsital, Inc., Boston, MA (US)

(72) Inventors: Mauricio Farez, Buenos Aires (AR); Francisco J. Quintana, Jamaica Plain, MA (US); Jorge Correale, Buenos Aires (AR)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 15/525,375

(22) PCT Filed: Nov. 12, 2015

(86) PCT No.: PCT/US2015/060488
§ 371 (c)(1),
(2) Date: May 9, 2017

(87) PCT Pub. No.: WO2016/077654
PCT Pub. Date: May 19, 2016

(65) Prior Publication Data
US 2017/0333371 A1  Nov. 23, 2017

Related U.S. Application Data

(60) Provisional application No. 62/078,473, filed on Nov. 12, 2014.

(51) Int. Cl.
| A61K 31/343 | (2006.01) |
| G01N 33/74 | (2006.01) |
| A61K 31/165 | (2006.01) |
| A61K 31/4045 | (2006.01) |
| A61K 45/06 | (2006.01) |
| C07D 209/16 | (2006.01) |

(52) U.S. Cl.
CPC .......... *A61K 31/165* (2013.01); *A61K 31/343* (2013.01); *A61K 31/4045* (2013.01); *A61K 45/06* (2013.01); *C07D 209/16* (2013.01); *G01N 33/74* (2013.01); *G01N 2800/285* (2013.01); *G01N 2800/50* (2013.01); *G01N 2800/52* (2013.01)

(58) Field of Classification Search
None
See application file for complete search history.

(56) References Cited

U.S. PATENT DOCUMENTS

| 8,389,739 B1 | 3/2013 | Thacher et al. | |
| 2002/0040018 A1 | 4/2002 | Jones | |
| 2006/0223877 A1* | 10/2006 | Zemlan | A61K 31/4045 514/419 |
| 2008/0167363 A1* | 7/2008 | Barlow | A61K 31/343 514/411 |

FOREIGN PATENT DOCUMENTS

| WO | 2006/105455 | 10/2006 |
| WO | 2013/033310 | 3/2013 |

OTHER PUBLICATIONS

Baker et al. , Critical appraisal of animal models of multiple sclerosis, Jun. 2011, Multiple Sclerosis Journal 17(6):647-657.*
Behan et al., The sad plight of multiple sclerosis research (low on fact, high on fiction): critical data to support it being a neurocristopathy, Sep. 24, 2010, Inflammopharmacol 18:265-290.*
Ransohoff, R. M., Animal models of multiple sclerosis: the good, the bad and the bottom line, Aug. 2012, Nature Neuroscience 15(8):1074-1077.*
'T Hart, et al., Modelling of multiple sclerosis: lessons learned in a non-human primate, Oct. 2004, The Lancet Neurology 3(10):588-597.*
Wekerle et al., Animal models of multiple sclerosis, 2006, Drug Discovery Today: Disease Models 3(4):359-367.*
Miller et al., Melatonin reduces oxidative stress in the erythrocytes of multiple sclerosis patients with secondary progressive clinical course , 2013, Journal of Neuroimmunology 257:97-101.*
Hardeland, R., Neurobiology, Pathophysiology, and Treatment of Melatonin Deficiency and Dysfunction, 2012, The Scientific World Journal vol. 2012, Article ID 640389, 18 pages, doi:10.1100/2012/640389 (Year: 2012).*
Álvarez-Sánchez et al., "Melatonin controls experimental autoimmune encephalomyelitis by altering the T effector/regulatory balance," Brain, Behavior and Immunity, 2015, 1-14.
Apetoh et al., "The aryl hydrocarbon receptor interacts with c-Maf to promote the differentiation of type 1 regulatory T cells induced by IL-27," Nat. Immunol, Sep. 2010, 11: 854-861.
Ascherio et al., "Epstein-Barr virus antibodies and risk of multiple sclerosis: a prospective study," Jama, 2001, 286: 3083-3088.
Ascherio et al., "The initiation and prevention of multiple sclerosis," Nature Reviews Neurology, Nov. 2012, 8: 602-612.
Ascherio et al., "Vitamin D and multiple sclerosis," The Lancet Neurology, 2010, 9: 599-612.
Ascherio et al., "Vitamin D as an Early Predictor of Multiple Sclerosis Activity and Progression," JAMA Neurol, 2014, 71: 306.
Astier et al., "Alterations in CD46-mediated Tr1 regulatory T cells in patients with multiple sclerosis," Journal of Clinical Investigation, Dec. 2006, 116: 3252-3257.
Awasthi and Kuchroo, "Th17 cells: from precursors to players in inflammation and infection," International Immunology, May 2009, 21: 489-498.
Baeten and Kuchroo, "Interleukin-17 and a tale of two autoimmune diseases," Nature Medicine, Jul. 2013, 19: 824-825.
Beecham et al., "Analysis of immune-related loci identifies 48 new susceptibility variants for multiple sclerosis," Nat Genet, Nov. 2013, 45: 1353-1360.
Brzezinski, "Melatonin in humans," N Engl J Med, 1997, 336: 186-195.

(Continued)

*Primary Examiner* — John D Ulm
(74) *Attorney, Agent, or Firm* — Fish & Richardson P.C.

(57) ABSTRACT

Methods for treating, or reducing risk of developing, seasonal worsening of multiple sclerosis (MS) in a subject who has MS, comprising administering a melatonin agonist to a subject.

12 Claims, 12 Drawing Sheets
Specification includes a Sequence Listing.

(56) References Cited

OTHER PUBLICATIONS

Castellano et al., "Nitric Oxide Affects ERK Signaling through Down-Regulation of MAP Kinase Phosphatase Levels during Larval Development of the Ascidian Ciona intestinalis," PLoS ONE, 2014, 9: e102907.
Chan et al., "Protein microarrays for multiplex analysis of signal transduction pathways," Nature Medicine, Dec. 2004, 10: 1390-1396.
Codarri et al., "RORγt drives production of the cytokine GM-CSF in helper T cells, which is essential for the effector phase of autoimmune neuroinflammation," Nat. Immunol, 2011, 12: 560-567.
Compston and Coles, "Multiple sclerosis," Lancet, Oct. 2008, 372: 1502-1517.
Correale and Farez, "Association between parasite infection and immune responses in multiple sclerosis," Ann. Neurol, 2007, 61: 97-108.
Correale et al., "Immunomodulatory effects of Vitamin D in multiple sclerosis," Brain, 2009, 132: 1146-1160.
Correale et al., "The risk of relapses in multiple sclerosis during systemic infections," Neurology, Aug. 2006, 67: 652-659.
Dong, "Targeting Th17 cells in immune diseases," Cell Research, 2014, 24:901-903.
El-Behi et al., "The encephalitogenicity of TH17 cells is dependent on IL-1- and IL-23-induced production of the cytokine GM-CSF," Nat. Immunol., Jun. 2011, 12: 568-575.
Farez et al., "Melatonin Contributes to the Seasonality of Multiple Sclerosis Relapses," Cell, 2015, 1338-1352.
Farez et al., "Sodium intake is associated with increased disease activity in multiple sclerosis," Journal of Neurosurg Psychiatry, Jan. 2015, 86: 26-31.
Farez et al., "Toll-like receptor 2 and poly(ADP-ribose) polymerase 1 promote central nervous system neuroinflammation in progressive EAE," Nat. Immunol, Sep. 2009, 10: 958-964.
Fassi et al., "[Seasonal variations in 25-hydroxyvitamin D in young and elderly and populations in Buenos Aires City]," Medicina, 2003, 63: 215-220 (with English abstract).
Gandhi et al., "Activation of the aryl hydrocarbon receptor induces human type 1 regulatory T cell-like and Foxp3(+) regulatory T cells," Nat. Immunol, Sep. 2010, 11: 846-853.
Graham et al., "Prediction of nocturnal plasma melatonin from morning urinary measures," J Pineal Res, 1998, 24, 230-238.
Han et al., "Th17 cells in autoimmune diseases," Frontiers of Medicine, Mar. 2015, 9(1):10-19.
Hedström et al., "Shift work at young age is associated with increased risk for multiple sclerosis," Ann. Neurol, Nov. 2011, 70: 733-741.
Hernan et al., "Cigarette smoking and the progression of multiple sclerosis," Brain, 2005, 128: 1461-1465.
Hickie and Rogers, "Novel melatonin-based therapies: potential advances in the treatment of major depression," Lancet, Aug. 2011, 378: 621-631.
Hurwitz., "The diagnosis of multiple sclerosis and the clinical subtypes," Ann Indian Acad Neurol., Oct.-Dec. 2009, 12(4): 226-230.
International Preliminary Report on Patentability in International Application No. PCT/US2015/060488, dated May 26, 2017, 11 pages.
Jetten, "Retinoid-related orphan receptors (RORs): critical roles in development, immunity, circadian rhythm, and cellular metabolism," Nucl Recept Signal, 2009, 7: e003.
Jin et al., "Seasonal patterns in optic neuritis and multiple sclerosis: a meta-analysis," Journal of the Neurological Sciences, 2000, 181: 56-64.
Jockers et al., "Melatonin receptors, heterodimerization, signal transduction and binding sites: what's new?," British Journal of Pharmacology, 2008, 154: 1182-1195.
Johnson, "Molecular stop signs: regulation of cell-cycle arrest by C/EBP transcription factors," J. Cell. Sci, 2005, 118: 2545-2555.
Karim et al., "Disposition kinetics and tolerance of escalating single doses of ramelteon, a high-affinity MT1 and MT2 melatonin receptor agonist indicated for treatment of insomnia," J Clin Pharmacol, 2006, 46: 140-148.
Kobayashi et al., "NFIL3-deficient mice develop microbiota-dependent, IL-12/23-driven spontaneous colitis," The Journal of Immunology, 2014, 192: 1918-1927.
Kojetin and Burris, "REV-ERB and ROR nuclear receptors as drug targets," Nat Rev Drug Discov, Mar. 2014, 13: 197-216.
Korn et al., "IL-17 and Th17 Cells," Annu. Rev. Immunol, 2009, 27: 485-517.
Lathrop et al., "Peripheral education of the immune system by colonic commensal microbiota," Nature, Oct. 2011, 478: 250-254.
Lee and Cua, "Melatonin Lulling Th17 Cells to Sleep," Cell, Sep. 2015, 162: 1212-1214.
Lee et al., "Induction and molecular signature of pathogenic TH17 cells," Nat. Immunol, Oct. 2012, 13: 991-999.
Lekstrom-Himes and Xanthopoulos, "Biological role of the CCAAT/enhancer-binding protein family of transcription factors," J. Biol. Chem, 1998, 273: 28545-28548.
Lin et al., Multiple Sclerosis, Spinal Cord Medicine, Principles and Practice Eds., Section V, Chapter 32, 2003, 429-440.
Løken-Amsrud et al., "Vitamin D and disease activity in multiple sclerosis before and during interferon-β treatment," Neurology, 2012, 79: 267-273.
Lopez-Diego and Weiner, "Novel therapeutic strategies for multiple sclerosis—a multifaceted adversary," Nat Rev Drug Discov, Nov. 2008, 7: 909-925.
López-González et al., "Melatonin treatment improves primary progressive multiple sclerosis: a case report," J Pineal Res, 2015, 13 pages.
Macchi and Bruce, "Human pineal physiology and functional significance of melatonin," Front Neuroendocrinol, 2004, 25: 177-195.
McDonald et al., "Recommended Diagnostic Criteria for Multiple Sclerosis: Guidelines From the International Panel on the Diagnosis of Multiple Sclerosis," Ann. Neurol, 2001, 50:121-127.
McGeachy et al., "TGF-β and IL-6 drive the production of IL-17 and IL-10 by T cells and restrain TH-17 cell-mediated pathology," Nat. Immunol, Dec. 2007, 8: 1390-1397.
McMullan et al., "Melatonin secretion and the incidence of type 2 diabetes," Jama, Apr. 2013, 309: 1388-1396.
Miossec et al., "Interleukin-17 and type 17 helper T cells," N Engl J Med, 2009, 361: 888-898.
Morera and Abreu, "Daytime/night-time and summer/winter melatonin and malondialdehyde rhythms: an inverse relationship," J Pineal Res, Oct. 2007, 43: 313-314.
Pévet, "Melatonin: from seasonal to circadian signal," J. Neuroendocrinol, 2003, 15: 422-426.
Polman et al., "Diagnostic Criteria for Multiple Sclerosis: 2005 Revisions to the McDonald Criteria." Ann Neurol, 2005, 58:840-846.
Polman et al., "Diagnostic criteria for multiple sclerosis: 2010 Revisions to the McDonald criteria," Ann. Neurol, 2011, 69: 292-302.
Pot et al., "Induction of regulatory Tr1 cells and inhibition of TH17 cells by IL-27," Seminars in Immunology, Dec. 2011, 23: 438-445.
Pozo et al., "Expression of the Mel1a-melatonin receptor mRNA in T and B subsets of lymphocytes from rat thymus and spleen," Faseb J 1997, 11: 466-473.
Pozo et al., "mRNA expression of nuclear receptor RZR/RORalpha, melatonin membrane receptor MT1, and hydroxyindole-O-methyltransferase in different populations of human immune cells," J Pineal Res, 2004, 37: 48-54.
Quintana et al., "Control of T(reg) and T(H)17 cell differentiation by the aryl hydrocarbon receptor," Nature, May 2008, 453: 65-71.
Roncarolo et al., "Interleukin-10-secreting type 1 regulatory T cells in rodents and humans," Immunol. Rev., Aug. 2006, 212: 28-50.
Rosecrans and Dohnal, "Seasonal vitamin D changes and the impact on health risk assessment," Clinical Biochemistry, 2014, 47: 670-672.

(56) References Cited

OTHER PUBLICATIONS

Rovaris et al., "Secondary progressive multiple sclerosis: current knowledge and future challenges," Lancet Neurol, Apr. 2006, 5: 343-354.
Runia et al., "Lower serum vitamin D levels are associated with a higher relapse risk in multiple sclerosis," Neurology, 2012, 79: 261-266.
Sakaguchi et al., "FOXP3+ regulatory T cells in the human immune system," Nature Reviews Immunology, Jul. 2010, 10: 490-500.
Saraiva and O'Garra, "The regulation of IL-10 production by immune cells," Nature Reviews Immunology, 2010, 10: 170-181.
Saraiva et al., "Interleukin-10 Production by Th1 Cells Requires Interleukin-12-Induced STAT4 Transcription Factor and ERK MAP Kinase Activation by High Antigen Dose," Immunity, 2009, 31: 209-219.
Sato et al., "A functional genomics strategy reveals Rora as a component of the mammalian circadian clock," Neuron, 2004, 43: 527-537.
Sawcer et al., "Genetic risk and a primary role for cell-mediated immune mechanisms in multiple sclerosis," Nature, Aug. 2011, 476: 214-219.
Schernhammer et al., "Epidemiology of urinary melatonin in women and its relation to other hormones and night work," Cancer Epidemiol. Biomarkers Prey, 2004, 13: 936-943.
Schumacher et al., "Problems of Experimental Trials of Therapy in Multiple Sclerosis: Report by the Panel on the Evaluation of Experimental Trials of Therapy in Multiple Sclerosis," Ann N Y Acad Sci., Mar. 1965, 122: 552-568.
Simpson et al., "Higher 25-hydroxyvitamin D is associated with lower relapse risk in multiple sclerosis," Ann. Neurol, 2010, 68: 193-203.
Sospedra and Martin, "Immunology of multiple sclerosis," Annu Rev. Immunol, 2005, 23: 683-747.
Spelman et al., "Seasonal variation of relapse rate in multiple sclerosis is latitude dependent," Ann. Neurol, 2014, 1-11.
Steinman, "Immunology of Relapse and Remission in Multiple Sclerosis," Annu Rev. Immunol, 2014, 32: 257-281.
Steinmayr et al., "staggerer phenotype in retinoid-related orphan receptor alpha-deficient mice," PNAS, 1998, 95: 3960-3965.
Tan and Lam, "Pharmacologic Inhibition of MEK-ERK Signaling Enhances Th17 Differentiation," The Journal of Immunology, 2010, 184: 1849-1857.
Ueno-Towatari et al., "Seasonal Variations of Melatonin Secretion in Young Females under Natural and Artificial Light Conditions in Fukuoka, Japan," J Physiol Anthropol, 2007, 26: 209-215.
Viglietta et al., "Loss of functional suppression by CD4+CD25+ regulatory T cells in patients with multiple sclerosis," J. Exp. Med, Apr. 2004, 199: 971-979.
Waite and Skokos, "Th17 response and inflammatory autoimmune diseases," International Journal of Inflammation, 2012, 2012: 819467, 10 pages.
Wiesenberg et al., "Transcriptional activation of the nuclear receptor RZR alpha by the pineal gland hormone melatonin and identification of CGP 52608 as a synthetic ligand," Nucleic Acids Res, 1995, 23: 327-333.
Wu et al., "Induction of pathogenic TH17 cells by inducible salt-sensing kinase SGK1," Nature, Apr. 2013, 496: 531-517.
Yang et al., "Metabolic response of mice to a postnatal ablation of CCAAT/enhancer-binding protein alpha," J. Biol. Chem, Nov. 2005, 280: 38689-38699.
Yang et al., "TH17 Lineage Differentiation Is Programmed by Orphan Nuclear Receptors RORα and RORγ," Immunity, Jan. 2008, 28: 29-39.
Yu et al., "TH17 cell differentiation is regulated by the circadian clock," Science, Nov. 2013, 342: 727-730.
Zambrano-Zaragoza et al., "Th17 Cells in Autoimmune and Infectious Diseases," Int J Inflam, 2014, 2014: 651503, 13 pages.
International Search Report and Written Opinion dated Jan. 29, 2016 in International Application No. PCT/US2015/060488, 20 pgs.
Lardone et al., "Melatonin Synthesized by T Lymphocytes as a Ligand of the Retinoic Acid-related Orphan Receptor," J. Pineal Res. 51: 454-462 (2011).
Farhadi et al., "Serum Levels of Melatonin and Cytokines in Multiple Sclerosis," Biomedical Journal 37: 90-92 (2014).
Adamczyk-Sowa et al., "Influence of Melatonin Supplementation on Serum Antioxidative Properties and Impact of the Quality of life in Multiple Sclerosis Patients," Journal of Physiology and Pharmacology 65(4):543-550 (2014).
Lin et al., "Modulation by Melatonin of the Pathogenesis of Inflammatory Autoimmune Diseases," Int. J. Mol. Sci. 14: 11747-11766 (2013).
European Search Report in Application No. 15858738.6, dated Jun. 12, 2018, 13 pages.
Fauber and Magnuson., "Modulators of the Nuclear Receptor Retinoic Acid Receptor-Related Orphan Receptor-[gamma] (ROR [gamma] or RORc)," Journal of Medicinal Chemistry, Jul. 2014, 57: 5871-5892.
Ferrarelli, "Remission by melatonin," Science Signaling, Sep. 2015, 8: EC276, 8 pages.
Kang et al., "Melatonin ameliorates autoimmune encephalomyelitis through suppression of intercellular adhesion molecule-1," Journal of Veterinary Science, Jan. 2001, 2: 85-89.
Maestroni, "The immunotherapeutic potential of melatonin," Expert Opinion on Investigational Drugs, Mar. 2001, 10: 467-476.
CN Office Action in Chinese Appln. No. 201580073200.2, dated Jul. 29, 2019, 14 pages (with English translation).
Aharoni et al., "Glatiramer acetate reduces Th-17 inflammation and induces regulatory T-cells in the CNS of mice with relapsing-remitting or chronic EAE," Journal of Neuroimmunology, 2010, 225:100-111.
Börnsen et al., "Effect of Natalizumab on Circulating CD4+ T-Cells in Multiple Sclerosis," PLOS One, Nov. 2012, 7(11):e47578, 11 pages.
Constantinescu et al., "Experimental autoimmune encephalomyelitis (EAE) as a model for multiple sclerosis (MS)," British Journal of Pharmacology, 2011, 164:1079-1106.
Glebezdina et al., "Role of Endogenous Melatonin in the Regulation of Th17/Treg Balance during Pregnancy," Bulletin of Experimental Biology and Medicine, 164(4):462-465, Feb. 2018.
McCarthy et al., "Mouse Models of Multiple Sclerosis: Experimental Autoimmune Encephalomyelitis and Theiler's Virus-Induced Demyelinating Disease," Methods Mol. Biol., 2012, 900:381-401MC.
Mehling et al., "Th17 central memory T cells are reduced by FTY720 in patients with multiple sclerosis," Neurology, Aug. 2010, 8 pages, vol. 75, Issue 5.
Vieria et al., "Glatiramer Acetate (Copolymer-1, Copaxone) Promotes Th2 Cell Development and Increased IL-10 Production Through Modulation of Dendritic Cells," The Journal of Immunology, 2003, 170:4483-4488.
Zhang et al., "Simvastatin Inhibits IL-17 Secretion by Targeting Multiple IL-17-Regulatory Cytokines and by Inhibiting the Expression of IL-17 Transcription Factor RORC in CD4+ Lymphocytes," The Journal of Immunology, 2008, 180:6988-6996.
Extended European Search Report in European Appln. No. 18210009. 9, dated Jun. 11, 2019, 13 pages.

\* cited by examiner

MELATONIN IN AUTOIMMUNE DISEASE

CLAIM OF PRIORITY

This application is a § 371 National Stage Application of PCT/US2015/060488, filed Nov. 12, 2015, which claims the benefit of U.S. Provisional Application Ser. No. 62/078,473, filed on Nov. 12, 2014. The entire contents of the foregoing are incorporated herein by reference.

FEDERALLY SPONSORED RESEARCH OR DEVELOPMENT

This invention was made with Government support under Grant Nos. AI093903 and NS087867 awarded by the National Institutes of Health. The Government has certain rights in the invention.

TECHNICAL FIELD

Described herein are methods for treating, or reducing risk of developing, seasonal worsening of multiple sclerosis (MS) in a subject who has MS, comprising administering a melatonin agonist to a subject.

BACKGROUND

Multiple Sclerosis (MS) is an immune-mediated disease of the central nervous system (CNS) thought to result from the destruction of myelin by autoreactive T cells. CD4$^+$ T cells characterized by the production of IFN-γ (Th1 cells) or IL-17 (Th17 cells) are considered important contributors to MS immunopathogenesis (Miossec et al., 2009; Sospedra and Martin, 2005; Steinman, 2014). FoxP3$^+$ regulatory T cells (Tregs) and IL-10 secreting type 1 regulatory T cells (Tr1) regulate the activity of effector T cells, accordingly deficits in Tregs and Tr1 cells have been described in MS (Astier et al., 2006; Sakaguchi et al., 2010; Viglietta et al., 2004). Thus, the balance between effector and regulatory T cells controls MS disease activity (Miossec et al., 2009; Sospedra and Martin, 2005; Steinman, 2014).

Genetic polymorphisms have been associated with MS risk and/or pathogenesis (Beecham et al., 2013; Sawcer et al., 2011). However, environmental factors such as infections (Ascherio et al., 2001; Correale and Farez, 2007; Correale et al., 2006), sodium intake (Farez et al., 2014), smoking (Hernan, 2005) and vitamin D levels (Ascherio et al., 2014) also affect MS development and course. Lower levels of vitamin D, for example, are associated with higher relapse rates (Runia et al., 2012; Simpson et al., 2010). As a result of the regulation of its synthesis by sun exposure, a significant seasonal fluctuation on vitamin D levels is observed in most locations, with a peak in spring-summer and a nadir in autumn and winter (Rosecrans and Dohnal, 2014). Thus, based on the reported anti-inflammatory effects of vitamin D (Correale et al., 2009) (Ascherio et al., 2010), MS relapse occurrence is predicted to peak during autumn and winter. However, several studies, including a meta-analysis (Jin et al., 2000) and a recent multicentric study (Spelman et al., 2014) found that MS disease activity is higher in spring and summer, suggesting that additional factors play a role in MS relapse seasonality.

SUMMARY

As described herein, melatonin levels, which peak in autumn-winter, show an inverse correlation with clinical disease activity in MS patients. Moreover, melatonin limits the development of EAE and controls Th17 and Tr1 cell differentiation. Thus, seasonal changes in melatonin levels may contribute to the decreased disease activity observed in autumn and winter through a mechanism mediated, at least partially, by the regulation of effector and regulatory T cells.

Thus, provided herein are methods for treating reducing risk of developing multiple sclerosis (MS), or for treating or reducing risk of developing, seasonal worsening of multiple sclerosis (MS) in a subject who already has MS. The methods include administering to a subject in need thereof a therapeutically effective amount of a melatonin agonist.

Also provided are methods for decreasing levels of Th17 cells and/or increasing levels of Tr1 cells in a subject, by administering to a subject in need thereof a therapeutically effective amount of a melatonin agonist. In some embodiments, the subject has an autoimmune disease, e.g., Multiple Sclerosis, Irritable Bowel Disease, Crohn's disease, spondyloarthritides, Systemic Lupus Erythematosus, Vitiligo, rheumatoid arthritis, psoriasis, Sjögren's syndrome, or diabetes, e.g., Type I diabetes.

In some embodiments, the methods include detecting a level of melatonin (e.g., 6-sulfatoxymelatonin (6-SM)) in a sample from a subject; comparing the level of melatonin in the sample to a reference level of melatonin that represents a level of melatonin in a control subject (e.g., a subject with MS) who has an increased risk of having or developing seasonal worsening of MS; and identifying the subject as having an increased risk of having or developing seasonal worsening of MS when the level of melatonin in the sample is below the reference level.

In some embodiments, the reference level of melatonin is or corresponds to 20, 20.5, 21, 21.5, 22, 22.5, 23, 23.5, or 24 ng/mg creatinine.

In some embodiments, the melatonin agonist is ramelteon ((S)—N-[2-(1,6,7,8-tetrahydro-2H-indeno[5,4-b] furan-8-yl)ethyl]propionamide), agomelatine (N-[2-(7-methoxynaphthalen-1-yl)ethyl]acetamide), tasimelteon ((1R, 2R)—N-[2-(2,3-dihydrobenzofuran-4-yl)cyclopropylmethyl]propanamide), or TIK-301 (LY-156735) (N-[(2R)-(6-Chloro-5-methoxy-1H-indol-3-yl)propyl]acetamide).

In some embodiments, the subject has a history of seasonal worsening of MS, has one or more symptoms associated with seasonal worsening of their MS, has low melatonin levels, lives in a climate where a low-melatonin season is occurring or about to occur, or lives in a climate where melatonin levels are typically low In some embodiments, the methods include administering a REV-ERB agonist or a ROR agonist.

In some embodiments, the melatonin agonist is administered orally, nasally, intravenously, or intrathecally.

Also provided herein are melatonin agonists for use in treating, or reducing risk of developing, seasonal worsening of multiple sclerosis (MS) in a subject who has MS.

In some embodiments, the subject has a level of melatonin below a reference level, e.g., a reference level of melatonin that is or corresponds to 20, 20.5, 21, 21.5, 22, 22.5, 23, 23.5, or 24 ng melatonin/mg creatinine.

In some embodiments, the melatonin agonist is ramelteon ((S)—N-[2-(1,6,7,8-tetrahydro-2H-indeno[5,4-b] furan-8-yl)ethyl]propionamide), agomelatine (N-[2-(7-methoxynaphthalen-1-yl)ethyl]acetamide), tasimelteon ((1R, 2R)—N-[2-(2,3-dihydrobenzofuran-4-yl)cyclopropylmethyl]propanamide), or TIK-301 (LY-156735) (N-[(2R)-(6-Chloro-5-methoxy-1H-indol-3-yl)propyl]acetamide).

In some embodiments, the subject has a history of seasonal worsening of MS, has one or more symptoms associated with seasonal worsening of their MS, has low melatonin levels, lives in a climate where a low-melatonin season is occurring or about to occur, or lives in a climate where melatonin levels are typically low In some embodiments, the melatonin agonist is in a composition comprising a REV-ERB agonist or a ROR agonist.

In some embodiments, the melatonin agonist is formulated to be administered orally, nasally, intravenously, or intrathecally.

In addition, provided herein are methods for identifying a subject for treatment with a melatonin agonist for reducing risk of developing, seasonal worsening of multiple sclerosis (MS). The methods include selecting a subject who has MS; detecting a level of melatonin (e.g., 6-sulfatoxymelatonin (6-SM)) in a sample from the subject; comparing the level of melatonin in the sample to a reference level of melatonin that represents a level of melatonin in a control subject (e.g., a subject with MS) who has an increased risk of having or developing seasonal worsening of MS; identifying the subject as having an increased risk of having or developing seasonal worsening of MS when the level of melatonin in the sample is below the reference level; and optionally administering a melatonin antagonist to the subject.

In some embodiments, the reference level of melatonin is or corresponds to 20, 20.5, 21, 21.5, 22, 22.5, 23, 23.5, or 24 ng/mg creatinine.

In some embodiments, the melatonin agonist is ramelteon ((S)—N-[2-(1,6,7,8-tetrahydro-2H-indeno[5,4-b] furan-8-yl)ethyl]propionamide), agomelatine (N-[2-(7-methoxynaphthalen-1-yl)ethyl]acetamide), tasimelteon ((1R, 2R)—N-[2-(2,3-dihydrobenzofuran-4-yl)cyclopropylmethyl]propanamide), or TIK-301 (LY-156735) (N-[(2R)-(6-Chloro-5-methoxy-1H-indol-3-yl)propyl]acetamide).

In some embodiments, the subject has a history of seasonal worsening of MS, has one or more symptoms associated with seasonal worsening of their MS, has low melatonin levels, lives in a climate where a low-melatonin season is occurring or about to occur, or lives in a climate where melatonin levels are typically low In some embodiments, the methods include administering a REV-ERB agonist or a ROR agonist.

In some embodiments, the melatonin agonist is administered orally, nasally, intravenously, or intrathecally.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Figure 1:
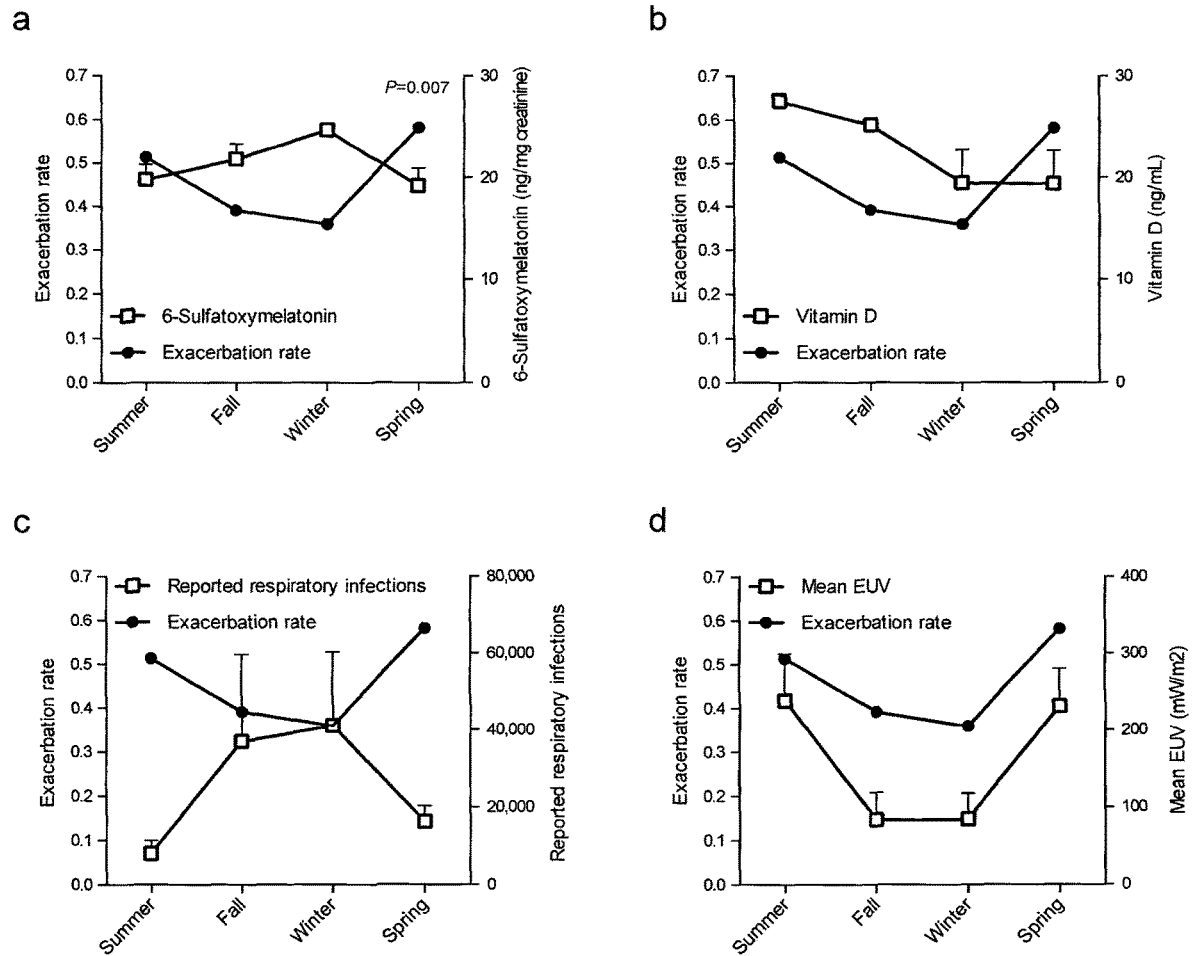
FIG. 1. Melatonin levels show an inverse correlation with MS clinical relapses. (a) Exacerbation rate for each season was estimated for the duration of the follow-up and depicted in the primary axis. 6-sulfatoxymelatonin levels measured in first morning urine in each season is depicted as mean±s.e.m. in secondary axis. P value corresponds to Poisson regression model. Lack of correlation between exacerbation rate and Vitamin D (b), reported respiratory infections (c), and UV radiation in Buenos Aires city (d). See also Table 1.

Strong epidemiological evidence supports a role of vitamin D in reducing MS relapses (Ascherio et al., 2012). Strikingly, vitamin D levels are higher during spring and summer, when relapse occurrence in MS patients peaks. Thus, the lower occurrence of relapses in seasons characterized by lower vitamin D levels represents a "seasonal paradox": relapses should be less frequent in spring and summer when vitamin D levels are higher, yet the opposite is found in most studies (Jin et al., 2000; Spelman et al., 2014), with a few exceptions (Loken-Amsrud et al., 2012). Our data may solve this paradox by identifying melatonin, whose levels are regulated by seasonal fluctuations in day length, as an additional regulator of the immune response in MS. Note that night shift work, which is associated with lower overall melatonin levels (Schernhammer et al., 2004), increases the risk of developing MS (Hedström et al., 2011). These findings suggest that melatonin may also be an MS risk factor; the relationship between melatonin levels and the risk of developing MS is the focus of ongoing investigations. Finally, the interplay between melatonin and other seasonal environmental factors known to impact MS such as vitamin D in different geographic locations remains to be further elucidated.

The rise in the past 50 years in the incidence of autoimmune disorders has reached an epidemic proportion and cannot be accounted by genetic risk only. Thus, increasing attention is being paid to environmental factors and their impact on the immune response and T cell differentiation in particular. For example: several compounds present in household products can activate the aryl hydrocarbon receptor and impact both Th17 and regulatory cell differentiation (Quintana et al., 2008); sodium in westernized diet and processed foods can enhance Th17 cell differentiation (Wu et al., 2013); the composition of commensal microbiota impacts T cell differentiation and response (Lathrop et al., 2011); and the lack of sun exposure and dietary habits can diminish vitamin D levels and affect regulatory T cell function (Correale et al., 2009). Each of these environmental factors acts on different signaling pathways, the study of the complex interactions between them can shed light on the effects of the environment on the immune system.

Pro-inflammatory Th17 cells are thought to contribute to the pathogenesis of EAE and MS (Miossec et al., 2009). Th17 cell differentiation is regulated by ROR-α and ROR-γt and therapies targeting Th17 cells are currently being tested in MS and other autoimmune diseases with preliminary encouraging results (Dominique L. P. Baeten and Kuchroo, 2013). Melatonin, despite having the potential to activate ROR-α, suppresses the generation of Th17 cells via its membrane receptor in a NFIL3-dependent fashion. Interestingly, it has been recently shown that the circadian clock suppresses Th17 development during nighttime through a similar NFIL3-dependent mechanism (Yu et al., 2013). Our work suggests that, in addition to Th17 cells, Tr1 cells are also regulated by melatonin during nighttime in an Erk1/2- and ROR-α dependent manner. Based on the high evolutionary conservation of melatonin production by the pineal gland and its regulation by daylight (Macchi and Bruce, 2004), it is likely that circadian and seasonal effects of melatonin on the immune response play a physiological role that drove its positive selection during evolution.

Tr1 cells are characterized by the production of IL-10 (Pot et al., 2011; Roncarolo et al., 2006). AhR, c-Maf and Erk1/2 regulate Tr1 cell development and IL-10 expression (Apetoh et al., 2010; Gandhi et al., 2010). The present work shows that melatonin promotes Tr1 cell differentiation by activating Erk1/2 signaling, which has been previously described to control IL-10 expression in T cells and DCs (Saraiva and O'Garra, 2010). We also identified ROR-α as a mediator of the effects of melatonin in Tr1 cells. Thus, these data suggest that melatonin utilizes multiple pathways to boost Tr1 cell differentiation.

The interplay between pro-inflammatory and regulatory cells controls the development of autoimmune diseases such as MS. Here we report that melatonin, whose levels show seasonal variability, control the balance between pathogenic and regulatory T cells. The present data identify melatonin-dependent signaling as a potential target for therapeutic immunomodulation.

Methods of Treatment

As shown herein, melatonin, whose levels show seasonal variability, can control the balance between pathogenic and regulatory T cells and improve autoimmune diseases in which the pathogenic Th17 T cells are present at increased levels and/or have increased activity, such as MS. Other autoimmune conditions that may benefit from treatment using the compositions and methods described herein include, but are not limited to, for example, Addison's Disease, alopecia, ankylosing spondylitis, antiphospholipid syndrome, autoimmune hemolytic anemia, autoimmune hepatitis, autoimmune oophoritis, Bechet's disease, bullous pemphigoid, celiac disease, chronic fatigue immune dysfunction syndrome (CFIDS), chronic inflammatory demyelinating polyneuropathy, Churg-Strauss syndrome, cicatricial pemphigoid, cold agglutinin disease, CREST Syndrome, Crohn's disease, diabetes (e.g., type I), dysautonomia, endometriosis, eosinophilia-myalgia syndrome, essential mixed cryoglobulinemia, fibromyalgia, syndrome/fibromyositis, Graves' disease, Guillain Barré syndrome, Hashimoto's thyroiditis, idiopathic pulmonary fibrosis, idiopathic thrombocytopenia purpura (ITP), inflammatory bowel disease (IBD), lichen planus, lupus, Ménière's disease, mixed connective tissue disease (MCTD), multiple sclerosis, myasthenia gravis, pemphigus, pernicious anemia, polyarteritis nodosa, polychondritis, polymyalgia rheumatica, polymyositis and dermatomyositis, primary agammaglobulinemia, primary biliary cirrhosis, psoriasis, Raynaud's phenomenon, Reiter's syndrome, rheumatic fever, rheumatoid arthritis, sarcoidosis, scleroderma, Sjögren's syndrome, spondyloarthropathy (spondyloarthritides), stiff-man syndrome, Takayasu arteritis, temporal arteritis/giant cell arteritis, autoimmune thyroid disease, ulcerative colitis, autoimmune uveitis, autoimmune vasculitis, vitiligo, and Wegener's granulomatosis. In some embodiments, the autoimmune disease is IBD, Crohn's disease, spondyloarthritides, Systemic Lupus Erythematosus, Vitiligo, rheumatoid arthritis, psoriasis, Sjögren's syndrome, or diabetes, e.g., Type I diabetes, all of which have been linked to Th17 cell dysfunction (see, e.g., Korn et al., Annu Rev Immunol. 2009; 27:485-517 Dong, Cell Research (2014) 24:901-903; Zambrano-Zaragoza et al., Int J Inflam. 2014; 2014: 651503; Waite and Skokos, International Journal of Inflammation; Volume 2012 (2012), Article ID 819467, 10 pages, dx.doi.org/10.1155/2012/819467; Han et al., Frontiers of Medicine 9(1):10-19 (2015).

The methods described herein include treatment of autoimmune diseases such as multiple sclerosis (MS) using an agonist of the melatonin receptor, e.g., of MTNR1A. Thus in some embodiments, the disorder is MS. The methods are particularly useful during the spring and summer months when melatonin levels are lower, but can be used at any time.

In some embodiments, once it has been determined that a person has an autoimmune disease, e.g., MS, then a treatment comprising administration of a therapeutically effective amount of a melatonin agonist can be administered. These methods can also include obtaining a sample from a subject, and evaluating the presence and/or level of melatonin in the sample, and comparing the presence and/or level with one or more references, e.g., a control reference that represents a normal level of melatonin, e.g., a level in a subject associated with winter months, and/or an affected reference that represents a level of melatonin associated with summer months. The presence of a level of melatonin below the reference level indicates that the subject should be treated with a melatonin agonist. These methods can also be used to predict whether someone will benefit from treatment with a melatonin agonist; a subject who has a level of melatonin below a reference level is more likely to benefit from treatment with a melatonin agonist than is a subject who has a level of melatonin above the reference level. In addition, the methods can be used for selecting a treatment for a subject; a treatment with a melatonin agonist is selected for a subject who has a level of melatonin below a reference level. In some embodiments, the subject has one or more symptoms associated with seasonal worsening of their autoimmune disease, e.g., MS, has low melatonin levels, lives in a climate where a low-melatonin season is occurring or about to occur, or lives in a climate where melatonin levels are typically low (e.g., a tropical climate).

Generally, the methods include administering a therapeutically effective amount of a melatonin agonist as described herein, to a subject who is in need of, or who has been determined to be in need of, such treatment. As used in this context, to "treat" means to ameliorate at least one symptom of the disorder associated with seasonal worsening of an autoimmune disease, e.g., MS. A treatment can result in a reduction in one or more symptoms of an autoimmune disease, e.g., MS, e.g., depression and fatigue, bladder dysfunction, spasticity, pain, ataxia, and intention tremor. A therapeutically effective amount can be an amount sufficient to prevent the onset of an acute episode or to shorten the duration of an acute episode, or to decrease the severity of one or more symptoms, e.g., heat sensitivity, internuclear ophthalmoplegia, optic neuritis, and Lhermitte symptom. In some embodiments, a therapeutically effective amount is an amount sufficient to prevent the appearance of, delay or prevent the growth (i.e., increase in size) of, or promote the healing of a demyelinated lesion in one or more of the brain, optic nerves, and spinal cord of the subject, e.g., as demonstrated on MRI.

Relapsing-Remitting and Progressive MS

Multiple Sclerosis (MS) is an inflammatory demyelinating disease of the central nervous system (CNS). MS is typically characterized clinically by recurrent or chronically progressive neurologic dysfunction, caused by lesions in the CNS. Pathologically, the lesions include multiple areas of demyelination affecting the brain, optic nerves, and spinal cord. The underlying etiology is uncertain, but MS is widely believed to be at least partly an autoimmune or immune-mediated disease.

In 85% of the patients MS initially follows a relapsing-remitting course (RRMS) in which acute autoimmune attacks against the central nervous system (CNS) are followed by a complete recovery (Compston and Coles, Lancet 372, 1502-1517 (2008)). The majority of the RRMS patients go on to develop secondary progressive MS (SPMS), characterized by a progressive, irreversible accumulation of neurological disability (Rovaris et al., Lancet Neurol 5, 343-354 (2006)). The progressive and irreversible disability that characterizes SPMS occurs in the absence of new inflammatory lesions, suggesting that other mechanisms might play a role in this stage of MS (Rovaris et al., Lancet Neurol 5, 343-354 (2006)). Although several therapies show positive effects on RRMS, they are usually ineffective in SPMS, and no markers are available to monitor the transition to SPMS. Indeed, treatments that halt the adaptive inflammatory response show positive effects on the management of RRMS but are usually ineffective in SPMS (Lopez-Diego and Weiner, Nat Rev Drug Discov 7, 909-925 (2008)). Thus, it is important to characterize the processes involved in the transition to SPMS, to identify new therapies for progressive MS and biomarkers to monitor the RRMS to SPMS transition.

Secondary Progressive Multiple Sclerosis (SPMS), one of four internationally recognized forms of Multiple Sclerosis (the others being Relapsing/Remitting Multiple Sclerosis, Primary Progressive Multiple Sclerosis and Progressive Relapsing Multiple Sclerosis), is characterized by a steady progression of clinical neurological damage with or without superimposed relapses and minor remissions and plateaus. People who develop SPMS will generally have previously suffered a period of Relapsing/Remitting Multiple Sclerosis (RRMS), which may have lasted from two to forty years or more. Occasionally the subject will have some relapses and remissions after the development of SPMS, but these tend to become less frequent over time.

Primary progressive MS (PPMS) is relatively rare (about 15% of the MS patient population), and features a slowly progressive loss in ability from onset of the disease. Most PPMS patients have progressive myelopathy or progressive cerebellar dysfunction.

A diagnosis of MS, and a determination of subtype, can be made using methods known in the art, e.g., on the basis of the presence of CNS lesions disseminated in space and time, and the elimination of alternative diagnoses (Problems of experimental trials of therapy in multiple sclerosis: Report by the panel on the evaluation of experimental trials of therapy in multiple sclerosis. Ann N Y Acad Sci. 122: 1965; 552-568). Alternatively, a diagnosis can be made based on the presence of clinical signs and symptoms including heat sensitivity, internuclear ophthalmoplegia, optic neuritis, and Lhermitte symptom (see, e.g., McDonald et al., Recommended Diagnostic Criteria for Multiple Sclerosis: Guidelines From the International Panel on the Diagnosis of Multiple Sclerosis. Ann. Neurol. 2001; 50:121; and Polman et al., Diagnostic Criteria for Multiple Sclerosis: 2005 Revisions to the "McDonald Criteria." Ann Neurol 2005; 58:840-846).

Methods of quantifying disability in MS include the Kurtzke Expanded Disability Status Scale (EDSS); MRI scanning; The Scripps Neurologic Rating Scale (SNRS); The Krupp Fatigue Severity Scale (FSS); The Incapacity Status Scale (ISS); The Functional Independence Measure (FIM); The Ambulation Index (AI); The Cambridge Multiple Sclerosis Basic Score (CAMBS); The Functional Assessment of Multiple Sclerosis (FAMS); Profile of Mood States (POMS); and the Sickness Impact Profile (SIP).

Further information about diagnosing and treating MS, and progressive MS, e.g., PPMS or SMPS, be found in the art, e.g., in Hurwitz et al., Ann Indian Acad Neurol. 2009 October-December; 12(4): 226-230; and Spinal Cord Medicine, Principles and Practice, Lin et al., Eds., (Demos Medical Publishing, Inc., 2003), e.g., Section V, Chapter 32, "Multiple Sclerosis". In general, the methods described herein can be practiced on any mammal, preferably a human.

Melatonin Agonists

Melatonin agonists useful in the methods described herein include, e.g., Melatonin (N-Acetyl-5-methoxytryptamine, CAS 73-31-4) (Sigma); Circadin/Neurin/PRM (also known as Prolonged Release Melatonin) (Neurim Pharmaceuticals Ltd) which treats insomnia, Agomelatine/Valdoxan/S-20098 ((N-[2-(7-Methoxy-1-naphthalenyl)ethyl]-acetamide; CAS 138112-76-2) (Servier Laboratories; Novartis) which is used as an antidepressant and is an agonist for both $MT_1$ and $MT_2$ receptors; N-Acetylserotonin (NAS); dimethoxy priopionamide 98 (Bristol Myers Squib); TAK-375/Ramelteon/Rozerem (N-[2-[(8S)-2,6,7,8-tetrahydro-1H-cyclopenta[e][1] benzofuran-8-yl]ethyl]propanamide; CAS 196597-26-9)) (Takeda Pharmaceutical Company Limited), Tasimelteon/Hetlioz (N-[[(1R,2R)-2-(2,3-dihydro-1-benzofuran-4-yl)cyclopropyl]methyl]propanamide)) (Vanda Pharmaceuticals) treats major depressive disorder. Luzindole (N-[2-(2-benzyl-1H-indol-3-yl)ethyl]acetamide) is a nonselective ligand with 15- to 25-fold higher affinity for the MT2 melatonin receptor and 4P-PDOT N-(4-phenyl-1,2,3,4-tetrahydronaphthalen-2-yl)propanamide or N-[(2S,4S)-4-phenyl-1,2,3,4-tetrahydronaphthalen-2-yl]propanamide or N-[(2R,4R)-4-phenyl-1,2,3,4-tetrahydronaphthalen-2-yl]propanamide) is a selective MT2 ligand; IIK7 (N-butanoyl-2-(2-methoxy-6H-isoindolo[2,1-a]indol-11-yl)-ethanamine (Sigma), Venlafaxine or Effexor (1-[2-(dimethylamino)-1-(4-methoxyphenyl)ethyl]cyclohexan-1-ol; hydrochloride); CAS 99300-78-4) (Sigma); and related SSRIs. Melatonin receptor antagonists also include the following: BMS-214778 (N-[[(1R,2R)-2-(2,3-dihydro-1-benzofuran-4-yl)cyclopropyl]methyl]propanamide); Sertaline 4 (1S,4S)-4-(3,4-dichlorophenyl)-N-methyl-1,2,3,4-tetrahydronaphthalen-1-amine; Paroxetine (3 S,4R)-3-(1,3-benzodioxol-5-yloxymethyl)-4-(4-fluorophenyl)piperidine; Fluoxetine (N-methyl-3-phenyl-3-[4-(trifluoromethyl)phenoxy]propan-1-amine); AMMTC (N-[(6-methoxy-9-methyl-1,2,3,4-tetrahydrocarbazol-4-yl)methyl] acetamide). Further examples of small molecule MT1 and 2 specific receptor agonists can be found in US20140011849; WO2007148808 (Melatonin (N-acetyl-5-methoxytryptamine)); US20090042861; WO2006107019A1 ((S)—N-[2-(1,6,7,8-tetrahydro-2H-indeno[5,4-b]furan-8-yl)ethyl]propionamide); U.S. Ser. No. 13/751,011; U.S. Ser. No. 14/688, 301 and US20140357710 ((N-[[(1R,2R)-2-(2,3-dihydro-1-benzofuran-4-yl)cyclopropyl]methyl]propanamide)); US20050164987/WO2005063297 (ML-23 or N-[2-(5-methoxy-1H-indol-3-yl)ethyl]-2,4-dinitroaniline); US20050137247 (LY-156735; BMS-214778); U.S. Pat. Nos. 8,859,593; 8,389,544; US20090209638, WO2007137247 and WO2011126948.

In some embodiments, the melatonin agonist is ramelteon ((S)—N-[2-(1,6,7,8-tetrahydro-2H-indeno[5,4-b] furan-8-yl)ethyl]propionamide), agomelatine (N-[2-(7-methoxynaphthalen-1-yl)ethyl]acetamide), tasimelteon ((1R, 2R)—N-[2-(2,3-dihydrobenzofuran-4-yl)cyclopropylmethyl]propanamide), or TIK-301 (LY-156735) (N-[(2R)-(6-Chloro-5-methoxy-1H-indol-3-yl)propyl]acetamide).

In some embodiments, the methods include administering an agonist of AA-NAT (Arylalkylamine N-acetyltransferase) and/or HIOMT (hydroxyindole-O-methyltransferase), which, among other activities, play a role in melatonin synthesis. These can include angiotensin receptor agonists such as L-162,313 ((5,7-dimethyl-2-ethyl-3-[[4-[2-(n-butyloxycarbonylsulfonamido)-5-isobutyl-3-thienyl]phenyl]methyl]-imadazo[4,5-b]pyridine)) and [Val5]-Angiotensin II acetate salt hydrate.

REV-ERB/ROR Agonists

In some embodiments, in addition to or as an alternative to a melatonin agonist, the methods include administration of an agonist of REV-ERB (e.g., of REV-ERBα and/or REV-ERBPβ) and/or of retinoic acid receptor-related orphan receptors (ROR, e.g., an agonist of RORα, RORPβ and/or RORγ), a number of which are known in the art. For example, the methods can include (or exclude) administration of a natural REV-ERB/ROR ligand, e.g., haem; Cholesterol/Cholesterol sulphate; 7α-hydroxycholesterol; 7β-hydroxycholesterol; 7-ketocholesterol; 20α-hydroxycholesterol; 22R-hydroxycholesterol; 25-hydroxycholesterol; 24S-hydroxycholesterol; 24R-hydroxycholesterol; 24,25-epoxycholesterol; Stearic acid; All-trans retinoic acid; Neoruscogenin; or (25S)-ruscogenin. Alternatively or in addition, the methods can include administration of a synthetic REV-ERB ligand, e.g., GSK4112, SR9009; SR9011; GSK2945; GSK0999; GSK5072; and/or GS2667; and/or a synthetic ROR ligand, e.g., T0901317; SR1078; SR3335 (also known as SR3335/ML176); SR1001; SR2211; SR1555; Digoxin; Ursolic acid; ML209; and/or a compound described in Zhang, W. et al. Mol. Pharmacol. 82, 583-590 (2012) (e.g., Compound 1a; Compound 1b: N-(4,6-dimethylbenzo[d]thiazol-2-yl)-3-methylthiophene-2-carboxamide; Compound 1c:N-(2-(4-ethylphenyl)-2H-benzo-[d][1,2,3]triazol-5-yl)propionamide; and/or Inhibitor Y:N-(5-benzoyl-4-phenylthiazol-2-yl)-2-(4-(ethylsulfonyl)phenyl)acetamide. See, e.g., Kojetin and Burris, Nature Reviews Drug Discovery 13, 197-216 (2014).

Standard Treatments

In some embodiments, a treatment described herein comprising a melatonin agonist is administered in combination with a standard treatment for MS, e.g., administration of corticosteroid therapy, interferon beta-1b, Glatiramer acetate, mitoxantrone, Fingolimod, teriflunomide, dimethyl fumarate, natalizumab, cannabis, or a combination thereof. In some embodiments, the treatment described herein is administered in combination with a treatment for one or more symptoms of MS, e.g., depression and fatigue, bladder dysfunction, spasticity, pain, ataxia, and intention tremor; such treatments include pharmacological agents, exercise, and appropriate orthotics. Additional information on the diagnosis and treatment of MS can be found at the National MS Society website, on the world wide web at nationalmssociety.org.

In some embodiments, where a subject is identified as having or likely to develop seasonal worsening of MS within a specific time period, e.g., as having a level of melatonin below a reference level, a treatment for progressive MS is administered, e.g., comprising mitoxantrone or natalizumab.

Pharmaceutical Compositions

The methods described herein include the manufacture and use of pharmaceutical compositions, which include melatonin agonists as active ingredients. Also included are the pharmaceutical compositions themselves.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

Pharmaceutical compositions are typically formulated to be compatible with the intended route of administration. Examples of routes of administration that are especially useful in the present methods include parenteral (e.g., intravenous), intrathecal, oral, and nasal or intranasal (e.g., by administration as drops or inhalation) administration. For compounds that don't cross the blood brain barrier, delivery directly into the CNS or CSF can be used, e.g., using implanted intrathecal pumps (see, e.g., Borrini et al., Archives of Physical Medicine and Rehabilitation 2014; 95:1032-8; Penn et al., N. Eng. J. Med. 320:1517-21 (1989); and Rezai et al., Pain Physician 2013; 16:415-417) or nanoparticles, e.g., gold nanoparticles (e.g., glucose-coated gold nanoparticles, see, e.g., Gromnicova et al. (2013) PLoS ONE 8(12): e81043). Methods of formulating and delivering suitable pharmaceutical compositions are known in the art, see, e.g., the books in the series Drugs and the Pharmaceutical Sciences: a Series of Textbooks and Monographs (Dekker, N.Y.); and Allen et al., Ansel's Pharmaceutical Dosage Forms and Drug Delivery Systems, Lippincott Williams & Wilkins; 8th edition (2004).

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

For oral administration, the compositions can be formulated with an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressured container or dispenser that contains a suitable propellant, e.g., a gas such as carbon dioxide, or a nebulizer. Such methods include those described in U.S. Pat. No. 6,468,798.

Therapeutic compounds that are or include nucleic acids can be administered by any method suitable for administration of nucleic acid agents, such as a DNA vaccine. These methods include gene guns, bio injectors, and skin patches as well as needle-free methods such as the micro-particle DNA vaccine technology disclosed in U.S. Pat. No. 6,194,389, and the mammalian transdermal needle-free vaccination with powder-form vaccine as disclosed in U.S. Pat. No. 6,168,587. Additionally, intranasal delivery is possible, as described in, inter alia, Hamajima et al., Clin. Immunol. Immunopathol., 88(2), 205-10 (1998).

Liposomes (e.g., as described in U.S. Pat. No. 6,472,375) and microencapsulation can also be used to deliver a compound described herein. Biodegradable microparticle delivery systems can also be used (e.g., as described in U.S. Pat. No. 6,471,996).

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811.

The pharmaceutical compositions can be included in a container, pack, or dispenser, e.g., single-dose dispenser together with instructions for administration. The container, pack, or dispenser can also be included as part of a kit that can include, for example, sufficient single-dose dispensers for one day, one week, or one month of treatment.

Dosage

Dosage, toxicity and therapeutic efficacy of the compounds can be determined, e.g., by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

An "effective amount" is an amount sufficient to effect beneficial or desired results. For example, a therapeutic amount is one that achieves the desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a composition depends on the composition selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the compositions described herein can include a single treatment or a series of treatments.

EXAMPLES

The invention is further described in the following examples, which do not limit the scope of the invention described in the claims.

Experimental Procedures

The following materials and methods were used in the Examples set forth below.

Patients.

Consecutive patients with relapsing-remitting MS according to McDonald criteria (Polman et al., 2011) were recruited from the MS clinic at the Rail Carrea Institute for Neurological Research (FLENI) between September and November of the same year. All patients lived in Buenos Aires City (latitude 34.6° S, longitude 58.4° W). Serum and first-morning urine were collected each season between 8 and 9 am during 2011-2012 and stored at −80° C. A second cohort of 26 relapsing-remitting MS patients was recruited between January and February of 2015 and serum and whole blood were collected between 8 and 9 am for CD4+ T cell isolation and melatonin measurement. For each sample, the exact date and time of collection and processing was recorded. Seasons were defined according to the southern hemisphere as follows: Summer (January-March), Fall (April-June), Winter (July-September), Spring (October-December). Study protocol was approved by the Institutional Ethics Committee, and all subjects signed an informed consent form.

Animals and EAE.

EAE was induced as follows: mice were immunized with 100 μg $MOG_{35-55}$ and 500 μg *Mycobacterium tuberculosis* extract H37Ra (Difco). Mice were also injected intraperitoneally with 200 ng pertussis toxin on days 0 and 2. Melatonin (5 mg/kg) or vehicle (0.01% DMSO) was administered daily at 7:00 PM.

Flow Cytometry Staining and Acquisition

For intracellular cytokine staining, cells were stimulated for 4 h at 37° C. with phorbol 12-myristate 13-acetate (50 ng/ml; Sigma), ionomycin (1 μg/ml; Sigma) and monensin (GolgiStop; 1 μg/ml; BD Biosciences). After being stained for surface markers, cells were fixed and made permeable according to the manufacturer's instructions (BD Biosciences). All antibodies against cytokines were from Biolegend. All experiments were started at the same time (8-9 am). Data were collected with a LSR II or FACSAria (BD Biosciences), then were analyzed with FlowJo software (Treestar).

Measurement of Cytokines.

Secreted cytokines were measured in tissue culture supernatants after 72-96 hs by enzyme-linked immunosorbent assay as previously described (Farez et al., 2009).

Quantitative RT-PCR.

RNA was extracted with RNAeasy columns (Qiagen, USA), then cDNA was prepared according to the manufacturer's instructions (Applied Biosystems) and was used as template for real-time PCR. All primers and probes were provided by Applied Biosystems and were used on the ViiA 7 Real-Time PCR System (Applied Biosystems). Expression was normalized to the expression of the housekeeping gene Gapdh.

Immunoblot Analysis.

For immunoblot analysis, cells were lysed with radioimmunoprecipitation buffer supplemented with protease inhibitor 'cocktail' (Sigma-Aldrich). Total lysates of the different T-cell subsets (40 fig) were resolved by electrophoresis through 4-12% Bis-Tris Nupage gels (Invitrogen, USA) and were transferred onto PVDF membranes (Millipore). The following primary antibodies were used: anti-ROR-α (Abcam); anti-MTNR1A (Santa Cruz), anti-total and phospho-Erk1/2 (Cell Signalling), anti-total C/EBP α (Cell Signaling), anti-phospho C/EBPα (Cell Signaling), anti-Nfil3 (Santa Cruz), and anti-GADPH (Abcam). Blots were developed with SuperSignal West Femto Maximum Sensitivity Substrate as suggested by the manufacturer (Pierce).

Clinical Data.

Clinical data were retrieved from our MS patient database. The number of relapses occurring from 2007 until 2012 was used to calculate monthly and season exacerbation rate. Exacerbation was defined as development of a new symptom or worsening of a preexisting symptoms confirmed by neurological examination, lasting at least 48 hours, and preceded by stability or improvement lasting at least 30 days.

Melatonin, Vitamin D, UVB and Infections Assessment.

Vitamin D levels were quantified at the clinical laboratory of the Rail Carrea Institute for Neurological Research (FLENI). 6-sulfatoxymelatonin (6-SM), which is the main melatonin metabolite and has an excellent correlation with night-time melatonin levels (Graham et al., 1998), was measured by ELISA as previously described (Graham et al., 1998) (Genway Biotech). For some experiments, serum melatonin was measured using a competitive ELISA kit (Genway Biotech). Official reports of upper respiratory tract infections in Buenos Aires city for the period studied were provided by governmental officials. UV incidence for Buenos Aires location was obtained from NASA satellites trough the Giovanni system (http://disc.sci.gsfc.nasa.gov/giovanni).

Animals and EAE.

MTNR1A and ROR-α knockout mice were purchased from Jackson Laboratories. C57BL/6 wild-type were purchased from the Faculty of Veterinary in La Plata University and Jackson Laboratories. NFIL3-deficient mice were provided by Chen Zhu; REV-ERBα deficient mice were provided by Mitch Lazar (University of Pennsylvania, Philadelphia, USA), and C/EBPα knockout mice were provided by Daniel Tenen (Beth Israel Deaconess Medical Center, Boston, USA). EAE was induced as follows: mice were immunized with 100 μg MOG35-55 (MEVGWYRSPFSRVVHLYRNGK (SEQ ID NO: 1)) and 500 μg *Mycobacterium tuberculosis* extract H37Ra (Difco). Mice were also injected intraperitoneally with 200 ng pertussis toxin on days 0 and 2. Melatonin (5 mg/kg) or vehicle (0.01% DMSO) was administered daily at 7:00 PM. All experiments were carried out in accordance with guidelines prescribed by the Institutional Animal Care and Use Committee (IACUC) at Harvard Medical School and IBYME.

Isolation of CNS Infiltrates.

CNS infiltrates were isolated as described (Mascanfroni et al., 2013). Mice were perfused with ice-cold PBS. The brain and spinal cord were removed and incubated in PBS containing collagenase type III (2 mg/ml; Worthington) and DNase (20 units/ml; Sigma-Aldrich). Tissues were then homogenized and loaded on a 30%-37%-70% Percoll gradient for enrichment of CNS infiltrates.

In Vitro Mouse T-Cell Differentiation.

Naive CD4+ T cells (CD4+CD44loCD62LhiCD25−) were from the spleen and lymph node of C57BL/6 wild-type, MTNR1A−, NFIL3−, REV-ERBα, C/EBPα-deficient or RORα-deficient mice using magnetic beads (CD4+ T cell isolation kit, Miltenyi Biotec). All experiments were started between 7 and 9 am. Cells were activated with plate-bound anti-CD3 (2 μg/ml; 14-0031-86; eBioscience) and anti-CD28 (2 μg/ml; 16-0281-86; eBioscience). Mouse IL-27 (30 ng/ml; 34-8271; Biolegend) was added for the generation of Tr1 cells. IL-6 (30 ng/ml; 406-ML-025; R&D Systems), TGF-β1 (15 ng/ml; 130-095-067; Miltenyi Biotec), anti-IL-4 (2.5 μg/ml; C17.8; Biolegend) and anti-IFN-γ (5 μg/ml; XMG1.2; Biolegend) were added for the generation of Th17 cells. Recombinant mouse IL-23 (30 ng/ml; 1887-ML-010; R&D Systems) was added at day 2. For some experiments IL-6 and IL-10 (10 ng/ml; 401-ML-025; R&D Systems) or TGF-β1 and IL-21 (100 ng/ml; 594-ML-010; R&D Systems) were used in instead for Th17 cell differentiation. IL-12 (30 ng/ml; 419-ML-010; R&D Systems) and anti-IL-4 (2.5 μg/ml; C17.8; Biolegend) were used for the generation of Th1 cells. IL-4 (30 ng/ml; 404-ML-010; R&D Systems) and anti-IFN-γ (5 μg/ml; XMG1.2; Biolegend) was added for the generation of Th2 cells. TGF-β1 (15 ng/ml; 130-095-067; Miltenyi Biotec) was used for the generation of Foxp3+ Tregs. Melatonin (Gador, Argentina), Agomelatin, and CGP-52608 (Sigma-Aldrich) were added at the start of the cultures and at day 2, at a final concentration of 2-20 ng/ml.

In vitro human T cell differentiation. For Th17 differentiation, naive CD45RA+ CD4+ T cells were isolated from PBMCs with magnetic beads (Naive Human CD4+ T Cell Isolation Kit II, Miltenyi Biotec) and seeded at a density of 5×10⁵ cells/ml in 24-well plates coated with anti-CD3 and (2 μg/ml) and soluble anti-CD28 and cultured in the presence of the following cytokines IL-1β (25 ng/ml), IL-6 (50 ng/ml), and TGF-β1 (2 ng/ml) and neutralizing antibodies to IFN-g (10 mg/ml) and IL-4 (10 microgram/ml). Alternatively, Th17 cells were differentiated by using IL-1β (25 ng/ml), IL-6 (50 ng/ml), and IL-23 (50 ng/ml) and neutralizing antibodies to IFN-g (10 mg/ml) and IL-4 (10 microgram/ml). For Th1 differentiation naïve CD4+T cells are cultured in the presence of IL-12 (20 ng/ml) and anti-IL-4 (10 μg/ml).

Measurement of Cytokines.

Secreted cytokines were measured in tissue culture supernatants after 72-96 hs by enzyme-linked immunosorbent assay as previously described (Farez et al., 2009).

Quantitative RT-PCR.

Primers-probe mixtures for mouse experiments were as follows (from Applied Biosystems; identifiers in parentheses): rorc (Mm01261022_m1), il23r (Mm00519942_m1), il10 (Mm0043614_m1), il17 (Mm00439619_m1), il21 (Mm00517640_m1), rora (Mm01173766_m1), rorc (Mm00441144_g1), foxp3 (Mm00475156_m1), tbx21 (Mm00450960_m1), gata3 (Mm00484683_m1), nr1d1 (Mm00520708_m1), nfil3 (Mm00600292_s1) and gapdh (Mm99999915_g1). Primers-probe mixtures for human experiments were as follows (from Applied Biosystems; identifiers in parentheses): RORC (Hs01076122_m1), IL17A (Hs00174383_m1), IL17F (Hs00369400_m1), IL10 (Hs00961622_m1), IFNG (Hs00989291_m1) and 18s (Hs03003631_g1).

Chromatin Immunoprecipitation.

DNA-protein complexes in cells were crosslinked with 4% paraformaldehyde and lysed with 0.35 ml lysis buffer (1% SDS, 10 mM EDTA and 50 mM Tris-HCl, pH 8.1) containing 1×protease inhibitor 'cocktail' (Roche Molecular Biochemicals). Chromatin was sheared by sonication and supernatants collected after centrifugation were diluted in buffer (1% Triton X-100, 2 mM EDTA, 150 mM NaCl and 20 mM Tris-HCl, pH 8.1). 5 μg antibody was prebound for a minimum of 6 hs to protein A and protein G Dynal magnetic beads (Invitrogen) and samples were washed three times with ice-cold PBS containing 5% BSA, and then were added to the diluted chromatin, followed by immunoprecipitation overnight. The magnetic bead-chromatin complexes were then washed three times in radioimmunoprecipitation buffer (50 mM HEPES, pH 7.6, 1 mM EDTA, 0.7% Na deoxycholate, 1% NP-40 and 0.5 M LiCl), followed by two washes with Tris-EDTA buffer. Immunoprecipitated chromatin was then extracted with a solution of 1% SDS and 0.1 MNaHCO3 and was heated at 65° C. for at least 6 h for reversal of the paraformaldehyde cross-linking. DNA fragments were purified with a QIAquick DNA purification Kit (Qiagen) and were analyzed by SYBR Green real-time PCR (Takara Bio).

Signaling Arrays.

Cells activated under polarizing conditions were treated with vehicle (DMSO 0.001%), melatonin (2-10 ng/mL), agomelatine (2-10 ng/mL) and CGP-52608 (2-10 ng/mL) during 72-96 hs and lysed. Lysates were transferred to 384-well polypropylene plates and were spotted onto Super Epoxi slides (Telechem) with a robotic microarrayer (Genetix) fitted with solid spotting pins. Slides were then probed, processed and analyzed as described (Farez et al., 2009).

Proliferation Assays.

Splenic cells were obtained from vehicle or melatonin treated WT mice 10 days after immunization with MOG35-55 and were re-stimulated in vitro for 3 days in the presence of MOG35-55. The cells were pulsed with [3H]thymidine (1 μCi/well) for the final 24 h. The frequency of T cells producing IL-17 (eBioscience), IFN-γ (BioLegend) or IL-10 (BD Pharmingen) and Foxp3+ T cells (eBioscience) was assessed by flow cytometry. For CFSE-based proliferation assay, CD4+ T cells were labeled with 1 μM CFSE (carboxyfluorescein diacetate succinimidyl ester; Molecular Probes). Data were acquired on an LSR III (BD Biosciences) or MacsQuants (Miltenyi) and analyzed with FlowJo software (TreeStar).

Plasmids.

The IL-10 promoter reporter and C-Maf and AhR vectors were previously described (Apetoh et al., 2010), vector expressing ROR-α were purchased from PlasmID at Harvard Medical School. Vectors coding for C/EBPα (44627) and Bmal reporter (46824) were purchased from Addgene. The retrovirus used for nfil3 overexpression in T cells was graciously provided by Laura Hooper (UT Southwestern, TX, USA). The retrovirus used for nr1d1 overexpression in T cells was graciously provided by Bart Staels (Institut Pasteur, Lille, France, USA). The nr1d1 promoter reporter was graciously provide by Vincent Laudent (Ecole Normale Supérieure, Lyon, France).

Transfection and Luciferase Assays.

HEK293 cells were grown in DMEM supplemented with 10% FBS and were transfected with FuGENE HD transfection reagent and 2 μg of each plasmids according the manufacturer's instructions (Roche). Firefly and *renilla luciferase* activity was analyzed 48 h after transfection and 24 h after treatment with a Dual Luciferase Assay kit (Promega).

Retroviral Transduction.

Retroviral expression constructs were transfected into human embryonic kidney HEK293T cells along with eco and gag-pol viral envelope constructs. Viral supernatants were collected at 72 h after transfection. Lentiviral transduction was performed by spinoculation at 1200 g for 1 hr at 32° C. in the presence of polybrene (8 μg/ml; Sigma).

T-Cell Transfer and Immunization.

Sorted splenic CD4+ T cells from C57BL/6, MTNR1A-, REV-ERBα and NFIL3-deficient mice were transferred i.p. (10×106 cells per mouse) into RAG-1 deficient mice. Ten days after transfer, mice were checked for reconstitution of CD4+ T cells and immunized with MOG35-55 in CFA. Twenty days after immunization, T cells were isolated and stained for cytokines.

Statistical Analysis.

A Poisson regression model was used to assess the impact of season, 6-SM levels and the number of clinical relapses, generating an incidence rate ratio (IRR) and corresponding 95% confidence intervals (CI). A repeated measures mixed model was used to assess the effect of treatment and its interaction with time in EAE experiments. A linear regression model was used to analyze the relationship between serum melatonin levels and IL-17 or IL-10 gene expression. Differences between two or more conditions were analyzed with Student's t test, Mann-Whitney test, One-way ANOVA or Wilcoxon Rank Sum test when appropriate. P values of less than 0.05 were considered significant. Unless otherwise specified, all data is presented as mean±SEM. All statistical analyses were performed using Stata v12 (Statacorp LP, Texas, USA).

Example 1. Melatonin Levels are Negatively Correlated with MS Clinical Relapses

We first established the seasonality of MS relapses in our cohort of 139 relapsing remitting MS patients (Table 1). Using a Poisson regression model, we detected a 32% reduction in the number of relapses occurring during fall and winter (incidence rate-ratio, IRR 0.682, 95% CI 0.49-0.95, P=0.02). Hence, the MS patient cohort used in this study shows the seasonality of MS relapses previously described for other cohorts (Jin et al., 2000; Spelman et al., 2014).

Melatonin production is stimulated by darkness and follows a seasonal pattern with higher levels during fall and winter (Brzezinski, 1997). Melatonin impacts several biological processes, including the circadian clock and the immune response (Brzezinski, 1997). Thus, we investigated the relationship between melatonin and MS disease activity by measuring 6-sulfatoxymelatonin (6-SM) levels in relapsing-remitting MS patients. Since 6-SM is the main melatonin metabolite, its levels in first morning urine are strongly correlated with nighttime melatonin secretion, supporting its use in epidemiological studies (Graham et al., 1998; McMullan et al., 2013). In agreement with previous reports (Morera and Abreu, 2007; Ueno-Towatari et al., 2007), we detected increased melatonin secretion during fall and winter, with lower levels during spring and summer (FIG. 1a and Table 1). Moreover, we found a significant negative correlation between 6-SM levels and MS exacerbation rates (P<0.01 Spearman's correlation). This was further confirmed in an age and gender-adjusted Poisson regression model, with a 3% reduction in the number of relapses for each 6-SM unit increase (IRR 0.97, 95% CI 0.95-0.99, P=0.007). Finally, to test whether the relationship between melatonin levels and exacerbation rate was synchronous, we lagged the occurrence of relapses for 1 (IRR 1.01, 95% CI 0.97-1.05; P=0.7), 2 (IRR 1.03, 95% CI 0.99-1.07; P=0.1), and 3 months (IRR 1.03, 95% CI 0.99-1.07; P=0.7), with no evidence of a lagged effect in relapse occurrence.

We also assessed vitamin D levels and, as previously reported for healthy controls and MS patients in our region (Correale et al., 2009; Fassi et al., 2003), overall levels were low throughout the year with higher levels during summer but no significant correlation with MS relapses (FIG. 1b). Finally, we did not detect a correlation between MS relapses and additional environmental factors such as reported upper respiratory tract infections and UV incidence, as determined by national registries and NASA satellites, respectively (FIG. 1c,d). Thus, higher melatonin levels during fall and winter are associated with a reduction in clinical relapses.

TABLE 1

Baseline and clinical characteristics of the study population

| | All participants (n = 139) |
|---|---|
| Age (years, mean ± SD) | 38.6 ± 10.9 |
| F:M (n) | 87:52 |
| Disease duration (years, median, range) | 6 (1-20) |
| EDSS (median, range) | 1 (0-4) |
| Treatment (n) | |
| None | 2 |
| Interferon | 64 |
| Glatiramer Acetate | 34 |
| Natalizumab | 2 |
| Fingolimod | 26 |
| Other | 11 |
| 6-SM levels (ng/mg creatinine, mean ± SEM) | |
| Summer | 19.8 ± 1.5 |
| Fall | 21.8 ± 1.6 |
| Winter | 24.7 ± 0.6 |
| Spring | 19.2 ± 1.7 |
| Vitamin D levels (ng/mL) | |
| Summer | 27.8 ± 0.8 |
| Fall | 25.2 ± 0.1 |
| Winter | 21.7 ± 3.2 |
| Spring | 21.7 ± 3.3 |

Example 2. Melatonin Ameliorates Experimental Autoimmune Encephalitis

Figure 7:
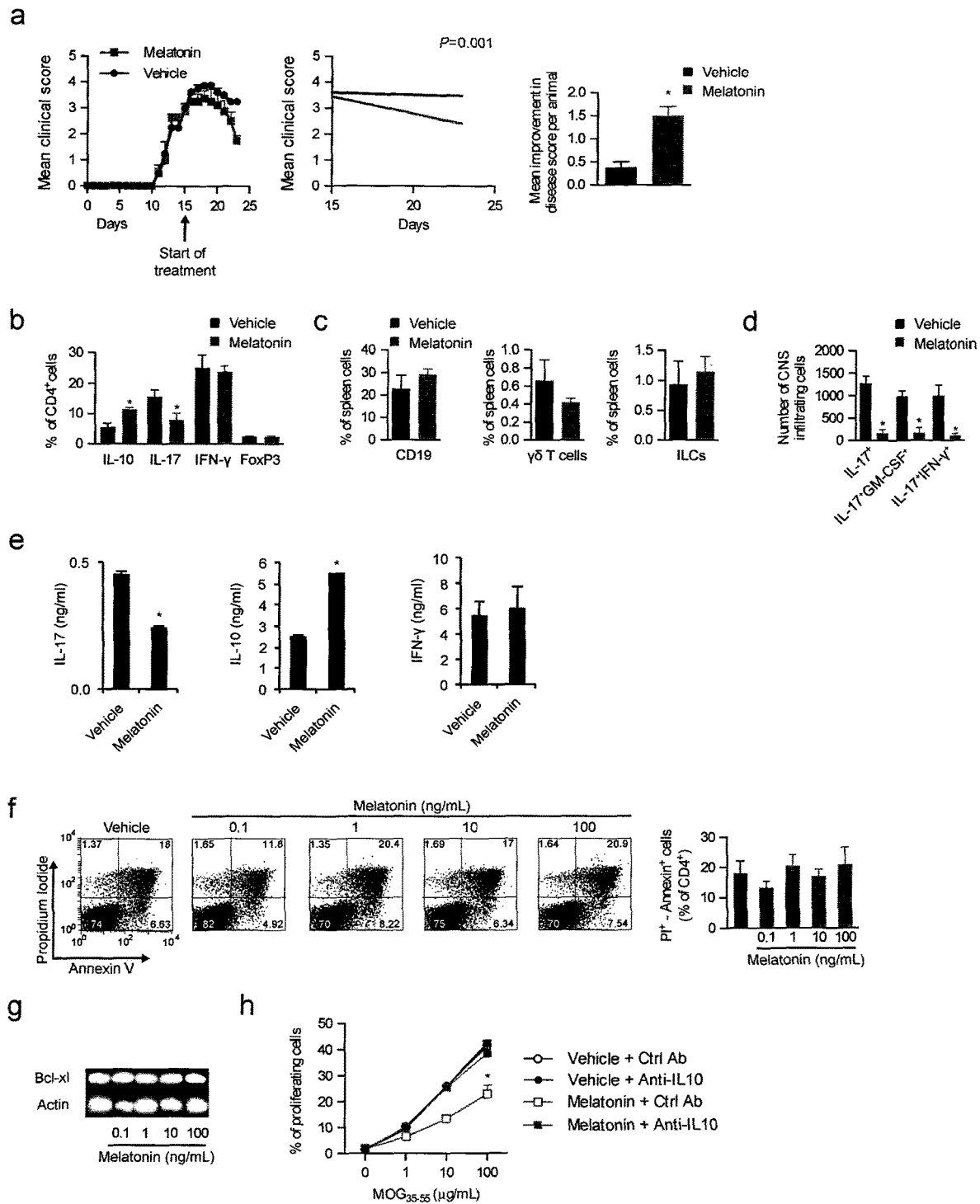
FIG. 7. Mechanisms Involved in Melatonin-Dependent EAE Amelioration, Related to FIG. 2 (A) EAE development in C57/B6 treated with vehicle (or melatonin (5 mg/kg) starting on day 15 after disease induction. Data are representative of two independent experiments (means and SEM) (nR10 mice/group). p value in middle panel corresponds for the effect of treatment in a repeated-measures mixed effect model. *p<0.05 of unpaired t test. (B) Flow cytometry analysis of IL-17+, IL10+, IFN-g+ and FoxP3+ CD4+ cells from the CNS of vehicle- or melatonin-treated mice at the peak of the disease. At least 4 mice were analyzed per group and data are presented as mean±SEM. *p<0.05 of unpaired t test. (C) Flow cytometry analysis of splenic CD19+ B cells, gd T cells and Lin-CD90+CD127+IL17+IL22+ innate lymphoid cells (ILCs) from vehicle or melatonin-treated mice at the peak of disease. At least 4 mice were analyzed per group and data are presented as mean±SEM. *p<0.05 of unpaired t test. (D) Flow cytometry analysis (total number) of IL-17+, IL-17+-IFN-g+, IL-17+-GM-CSF+CD4+ T cells from the CNS of control- or melatonin-treated mice at the clinical peak of EAE *p<0.05 of unpaired t test. (E) IL17, IL-10, and IFN-g in supernatants of 2D2+ T cells cultured in vitro in the presence of antigen presenting cells and MOG35-55 peptide. Data are representative of two independent experiments (means and SEM) *p<0.05 of unpaired t test. (F) Flow cytometry analysis of propidium iodide+ and annexin V+CD4+T cells after stimulation with antibodies CD3 and CD28 in the presence of vehicle or melatonin for 3 days. Data are representative of two independent experiments (means and SEM). *p<0.05 of unpaired t test. (G) Immunoblot analysis of Bcl-xl and actin in CD4+T cells activated as described in (F) in the presence of vehicle and melatonin 20 ng/ml. Data are representative of two independent experiments (means and SEM). (H) Proliferative response of CD4+ T cells stimulated with antibodies to CD3 and CD28 in the presence of melatonin and control or IL-10 blocking antibodies. Data are representative of three independent experiments (means and SEM)*p<0.05 of one-way ANOVA.
Figure 8:
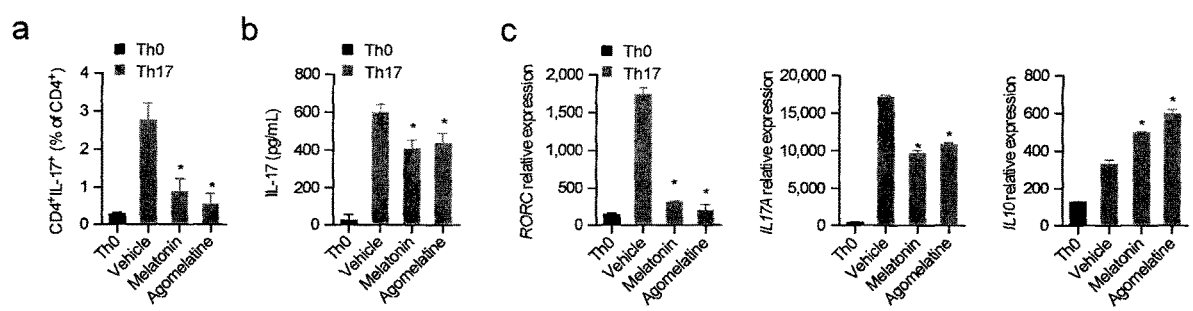
FIG. 8. Melatonin Interferes with Human Th17 Cell Differentiation, Related to FIG. 3 (A) Flow cytometry analysis of IL-17 expression in human Th17 differentiated CD4+ T cells (IL-1b, IL-6 and IL-23) in the presence or absence of melatonin (500 ng/ml) and agomelatine (500 ng/ml). Data are representative of three independent experiments (means and SEM) *p<0.05 of one-way ANOVA. (B) Cytokine quantification by ELISA of IL-17 in human Th17 differentiated CD4+ T cells in the presence or absence of melatonin (500 ng/ml) and agomelatine (500 ng/ml) as in a. Data are representative of three independent experiments (means and SEM) *p<0.05 of one-way ANOVA. (C) RT-PCR analysis of Th17 cells cultured as in a. Data are representative of three independent experiments (means and SEM) *p<0.05 of one-way ANOVA.

Based on our epidemiological findings, we studied the effects of melatonin on CNS inflammation using the experimental autoimmune encephalitis (EAE) model of MS. Naïve C57BL/6 wild-type mice were immunized with $MOG_{35-55}$ and treated daily with melatonin (5 mg/kg, intraperitoneally) or vehicle. Melatonin administration ameliorated EAE clinical symptoms (FIG. 2a, Table 2 and FIG. 7a). The amelioration of EAE was associated with a decreased number and frequency of Th17 cells in spleen, lymph nodes and CNS; this decrease was also detected in $IL-17^+$ $IFN\gamma^+$ and $IL-17^+$ $GM-CSF^+$ CD4+ T cells that have been associated to the pathogenesis of EAE (Codarri et al., 2011; El-Behi et al., 2011; Lee et al., 2012a) (FIG. 2c,d). We also detected a concomitant increase in IL-10 secreting CD4+ T cells; no significant changes were detected in the number or frequency of other T cell subsets, B cells, γδ T cells or innate lymphoid cells (ILCs) (FIG. 2b and FIG. 7b-d).

To further characterize the effects of melatonin on the encephalitogenic T-cell response, we analyzed the recall response to $MOG_{35-55}$. Splenocytes from melatonin-treated mice showed a diminished proliferative response to $MOG_{35-55}$, reduced IL-17 concomitant with increased IL-10 production, however no significant effects were detected on IFN-γ production (FIG. 2e,f). Thus, melatonin arrests the encephalitogenic Th17 cell response.

To investigate if melatonin acts directly on T cells or whether it controls the T-cell response indirectly through its effects on antigen presenting cells, we co-incubated sorted $CD4^+$ T cells from melatonin-treated or control mice with treatment-switched dendritic cells (DCs). When compared to controls isolated from vehicle-treated mice, CD4+ T cells from melatonin-treated mice co-incubated with splenic DCs isolated from control mice showed decreased proliferation and IL-17 secretion, concomitant with increased IL-10 production, (FIG. 2g,h). Conversely, we did not detect significant differences when we used DCs isolated from melatonin or vehicle treated mice to activate CD4+ T cells from control-treated mice.

In support for a direct effect of melatonin on T cells, melatonin suppressed the in vitro activation of naive $2D2^+$ transgenic T cells with $MOG_{35-55}$ and DCs (FIG. 2i, FIG. 7e) or with antibodies to CD3 and CD28 in the absence of DCs (FIG. 2j). Pretreatment of DCs with melatonin did not affect their ability to activate 2D2+ T cells in the presence of $MOG_{35-55}$ (FIG. 2k). Melatonin did not increase apoptosis in CD4+ T cells stimulated with antibodies against CD3 and CD28, as indicated by the analysis of annexin V and propidium iodide staining by flow cytometry or the expression of Bcl-xl levels (FIG. 7f,g). IL-10 blockade, however, abrogated the suppressive effects of melatonin on T-cell proliferation (FIG. 7h).

TABLE 2

Clinical features of EAE, Related to FIG. 2a

| Group | Incidence (%) | Mortality | Mean onset day (mean ± sd) | Mean maximum score (mean ± sd) |
|---|---|---|---|---|
| Vehicle | 17/20 (87.5%) | 0/20 | 12.8 ± 3.2 | 3.05 ± 1.4 |
| Melatonin | 17/24 (65%)* | 0/24 | 11.8 ± 3.0 | 2.06 ± 0.8** |

*P = 0.05
**P < 0.05

Example 3. Melatonin Affects Human T-Cell Differentiation

Figure 3:
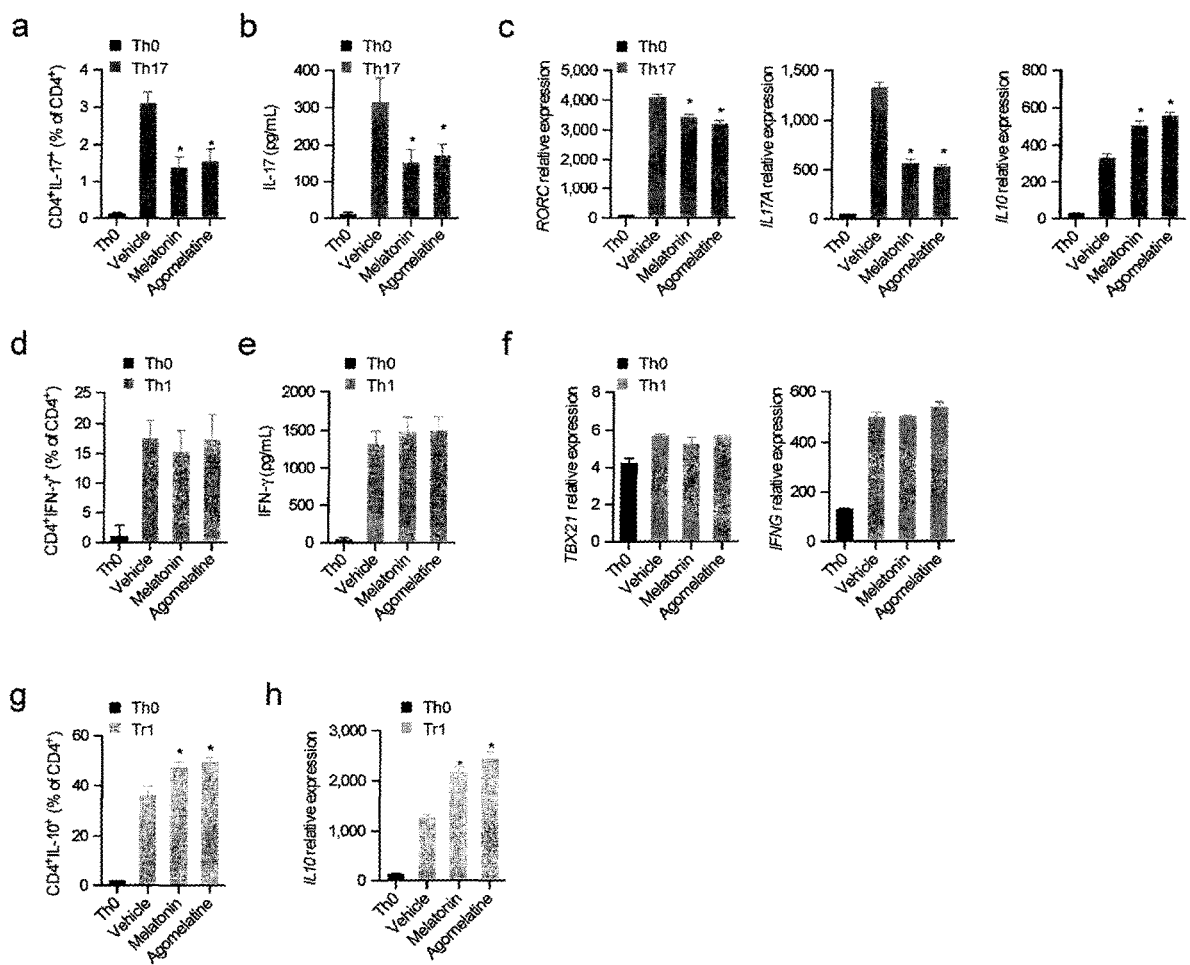

We then studied the effects of melatonin on human $CD4^+$ T cells. In addition, we also analyzed the effects of agomelatine, which activates melatonin-dependent signaling (Hickie and Rogers, 2011). Based on the effects of melatonin administration on T cells during EAE, we focused our studies on human Th17 and Tr1 cells. Melatonin and agomelatine reduced the production of IL-17, RORC and IL17A expression by human $CD4^+$ T cells activated under Th17 polarizing conditions (FIGS. 3a-c and FIG. 8), no effect was detected on the differentiation of human Th1 cells (FIGS. 3d-f). Concomitantly, melatonin and agomelatine increased IL10 expression. Indeed, melatonin and agomelatine also increased IL-10 production by human $CD4^+$ T cells activated under Tr1 polarizing conditions (FIG. 3g,h).

To further investigate the role of melatonin on the immune response in MS, we analyzed the correlation between serum melatonin levels and IL17 and IL10 expression in peripheral $CD4^+$ T cells of 26 RRMS patients (Table 3). Using an age- and gender-adjusted linear regression model we detected a negative correlation between melatonin in serum and IL17 expression in peripheral $CD4^+$ T cells (P=0.012): higher serum melatonin levels were associated to lower IL17 expression (Table 4). Conversely, linear regression analysis identified a positive correlation between higher IL10 expression in peripheral $CD4^+$ T cells and melatonin in serum (P=0.003). We did not detect a significant correlation between melatonin levels and the expression of RORC, NR1D1 or NFIL3 in $CD4^+$ T cells (Table 4). Thus, melatonin modulates the differentiation of human Th17 and Tr1 cells in vitro, and endogenous melatonin levels are associated to the expression levels of IL17 and IL10 in peripheral $CD4^+$ T cells in RRMS patients.

TABLE 3

Baseline and clinical characteristics of the MS cohort used for expression studies

|  | All participants (n = 26) |
| --- | --- |
| Age (years, mean ± SD) | 38 ± 9.24 |
| F:M (n) | 13:13 |
| Disease duration (years, median, range) | 5 (1-14) |
| EDSS (median, range) | 1 (0-4) |
| Treatment (n) |  |
| Interferon | 6 |
| Glatiramer Acetate | 4 |
| Fingolimod | 11 |
| Other | 5 |

TABLE 4

Correlation between melatonin levels and IL10 and IL17F in CD4+ cells isolated from MS patients.

| Variable | Coefficient | Standard Error | 95% CI | P value |
| --- | --- | --- | --- | --- |
| IL10 | 0.009 | 0.00053 | 0.007-0.011 | 0.003 |
| IL17 | −3.92 | 0.89 | −6.4--1.4 | 0.012 |
| RORC | 0.001 | 0.00111 | −0.004-0.003 | 0.387 |
| NR1D1 | 0.00000951 | 0.0000625 | −0.0002-0.0001 | 0.882 |
| NFIL3 | 0.00013 | 0.00008 | −0.00006-0.0003 | 0.163 |

Example 4. Melatonin Interferes with Th17 Generation

Figure 4:
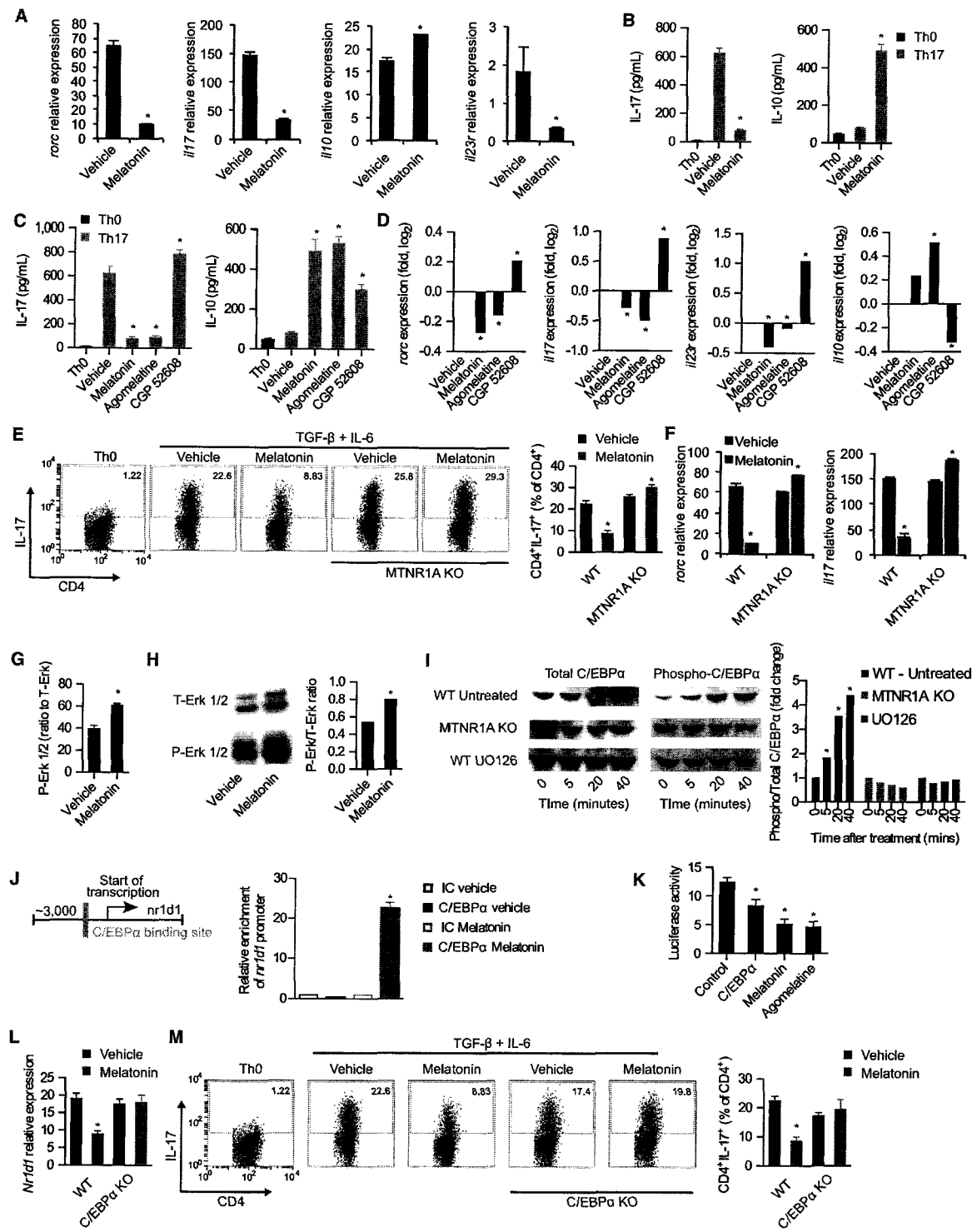
FIG. 4. Melatonin interferes with Th17 cell differentiation via the Erk1/2-C/EBPα pathway. (a) CD4+ naïve T cells were differentiated into Th17 cells by the addition of TFG-α, IL-6 (0 h) and IL-23 (48 hs) in the presence or absence of melatonin (2 ng/ml) and analyzed by RT-PCR after 72 hs. Displayed image is representative of five experiments. * P<0.05 of unpaired T-test (b) Cytokine secretion analysis of IL-17 and IL-10 after 72 hs of culture as in a. Data are representative of three independent experiments (means and s.e.m.)* P<0.05 of unpaired T-test (c) Cytokine secretion in Th17 differentiated CD4+ T cells in the presence or absence of melatonin (2 ng/ml), agomelatine (20 ng/ml, MTNR1A ligand) and CGP 52608 (20 ng/ml, ROR-α ligand). Data are representative of three independent experiments (means and s.e.m.). * P<0.05 of one-way ANOVA. (d) RT-PCR analysis of Th17 cells cultured as in c. Data are representative of three independent experiments (means and s.e.m.). * P<0.05 of one-way ANOVA. (e) Flow cytometry analysis of IL-17 expression as in a, in wild type mice and MTNR1A-deficient mice. Data are representative of three independent experiments (means and s.e.m.) * P<0.05 of unpaired T-test. (f) Quantitative PCR analysis of wild type and MTNR1A deficient mice cultured as in e. Data are representative of three independent experiments (means and s.e.m.)* P<0.05 of unpaired T-test. (g) Signal transduction profiling using reverse protein arrays. Data are representative of two independent experiments (means and s.e.m.)* P<0.05 of unpaired T-test. (h) Immunoblot analysis of T- and P-Erk1/2. Data are representative of two independent experiments (means and s.e.m.). (i) Immunoblot analysis of T- and P-C/EBPα Data are representative of two independent experiments (means and s.e.m.). (j) Putative binding sites of C/EBPα in nr1d1 (left panel); chromatin immunoprecipitation with anti-C/EBPα (right panel). Data are representative of three independent experiments (means and s.e.m.) * P<0.05 of one-way ANOVA. (k) Luciferase activity of HEK-293 cells transfected with a luciferase reporter construct for the nr1d1 promoter. Data are representative of three independent experiments (means and s.e.m.)* P<0.05 of unpaired T-test. (1) Flow cytometry analysis of IL-17 expression as in a, in wild type mice and C/EBPα-deficient mice. Data are representative of two independent experiments (means and s.e.m.) * P<0.05 of one-way ANOVA. (M) Flow cytometry analysis of IL-17 expression as in (A), in wild-type mice and C/EBPα-deficient mice. Data are representative of three independent experiments (means and SEM). *p<0.05 of unpaired t test. See also FIG. 9-10.
Figure 9:
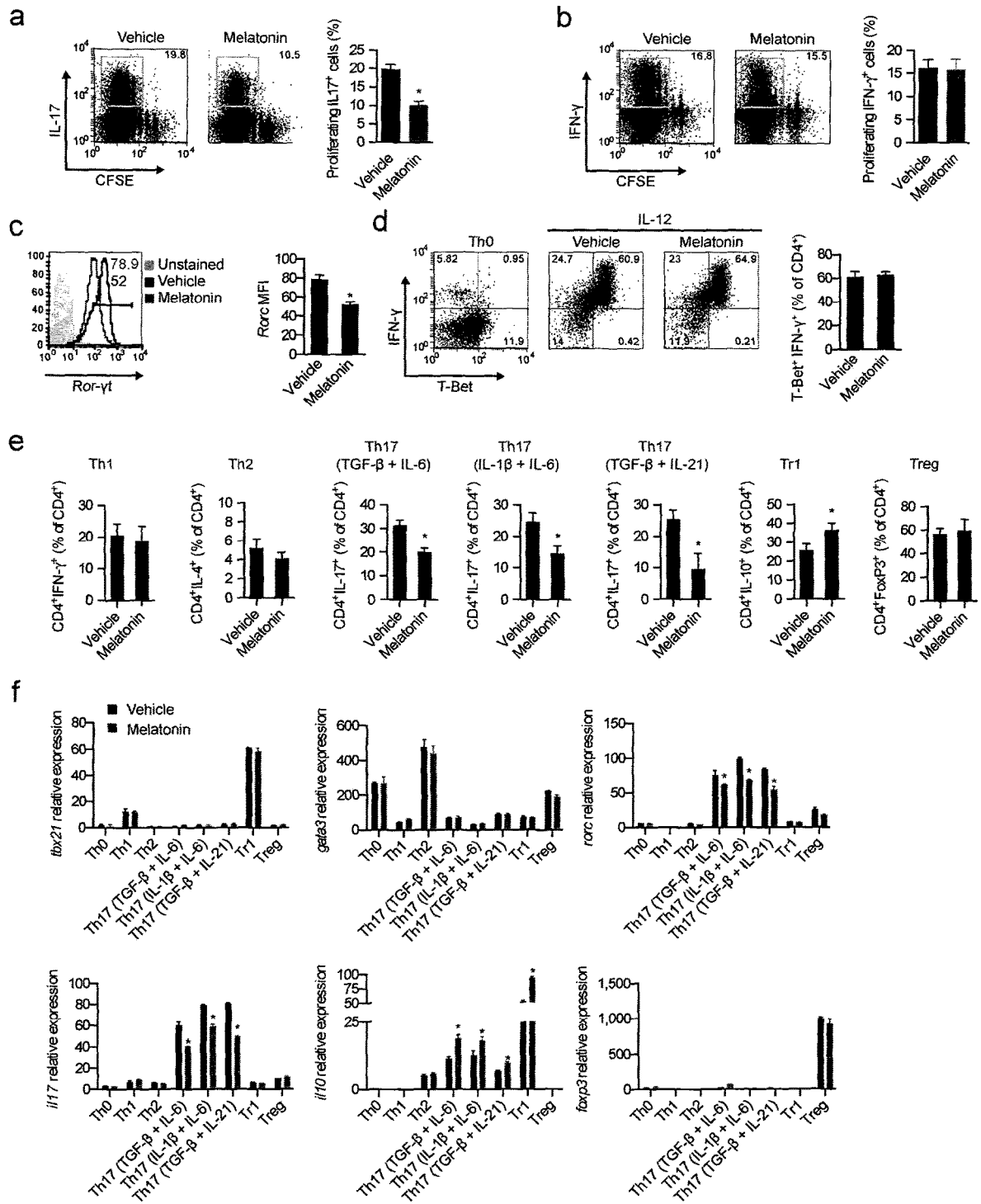
FIG. 9. Melatonin Selectively Interferes with Th17 Cell Differentiation and Boosts Tr1 Generation, Related to FIG. 4 (A and B) Flow cytometry analysis of proliferative response of CD4+T cells activated for 3 days under Th17 (A) or Th1 (B) polarizing conditions in the presence of vehicle or melatonin (2 ng/ml). Data are representative of three independent experiments (means and SEM)*p<0.05 of one-way ANOVA. (C) Flow cytometry analysis of RORgt expression in CD4+T cells activated for 3 days under Th17-polarizing conditions in the presence of vehicle or melatonin (2 ng/ml). Data are representative of three independent experiments (means and SEM)*p<0.05 of unpaired t test. (D) Flow cytometry analysis of T-bet expression in CD4+ T cells activated for 3 days under Th1-polarizing conditions in the presence of vehicle or melatonin (2 ng/ml). Data are representative of three independent experiments (means and s.e.m.). (E) Flow cytometry analysis of CD4+ naive T cells activated for 3 days under polarizing conditions favoring the differentiation of Th1, Th2, Th17, Tr1 and FoxP3+ iTreg cells, with or without the addition of melatonin (2 ng/ml). Data are representative of three independent experiments (means and SEM)*p<0.05 of unpaired t test. (F) RT-PCR analysis of gene expression in CD4+ T cells cultured as described in (E). Data are representative of two independent experiments (means and SEM). *p<0.05 of unpaired t test.

Together with Th1 cells, Th17 cells are thought to contribute to the pathogenesis of MS and EAE (Korn et al., 2009). Based on the suppressive effects of melatonin on EAE and IL-17 production by CD4+ T cells, we studied the effects of melatonin on murine Th17 cell differentiation. Melatonin interfered with the differentiation of Th17 cells in vitro as indicated by the expression of rorc, IL-17, and the IL-23 receptor necessary for the differentiation of Th17 cells into fully pathogenic cells; no effects were detected on the differentiation of FoxP3+ iTregs, Th1 or Th2 cells. (FIG. 4a,b and FIG. 9) (Lee et al., 2012b). Melatonin also increased the expression of IL-10, associated to non-pathogenic Th17 cells (Lee et al., 2012b; McGeachy et al., 2007) (FIG. 4a,b).

Figure 10:
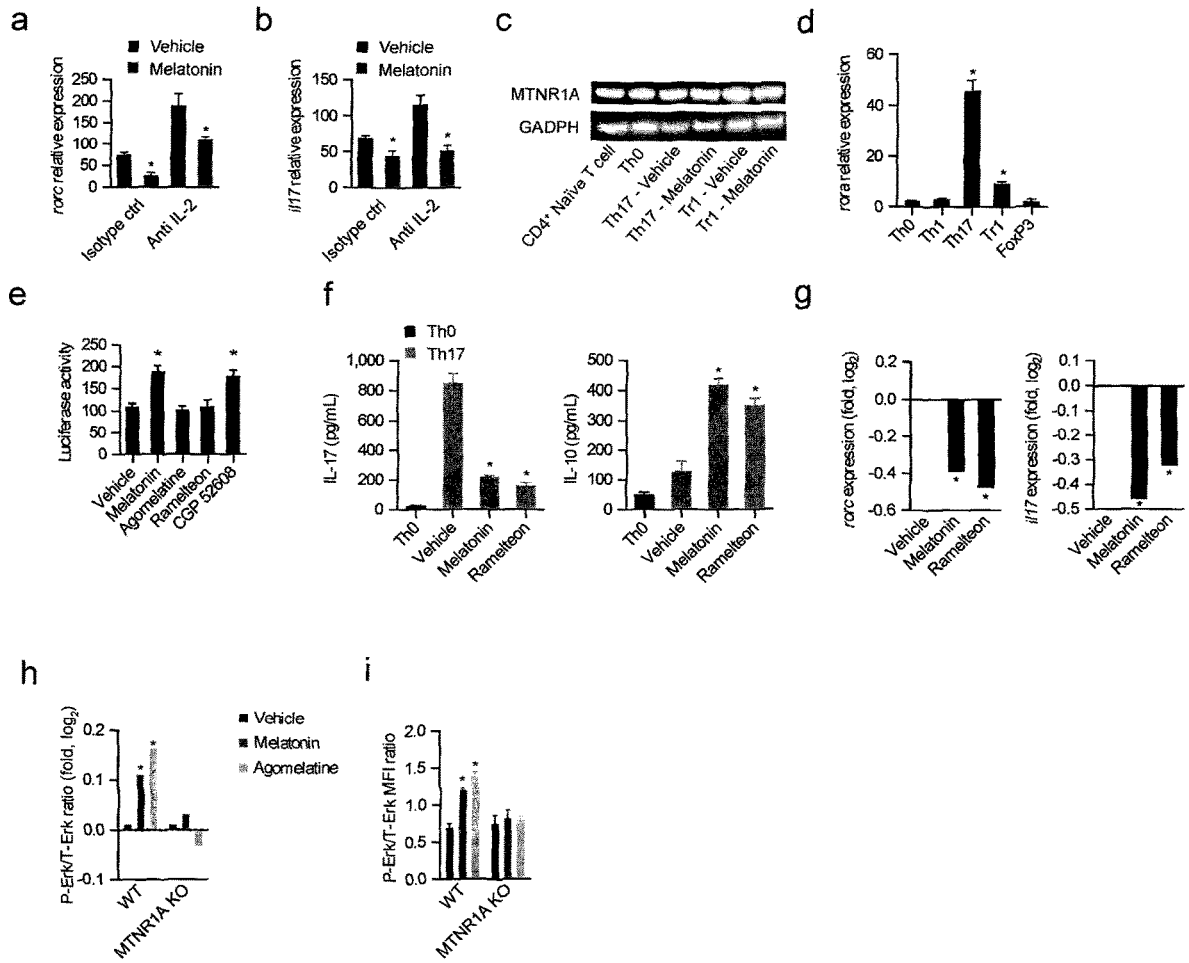
FIG. 10. Melatonin and Related Drugs Affect Th17 Cell Differentiation, Related to FIG. 4 (A and B) RT-PCR analysis of rorc (A) and il17 (B) expression in CD4+ T cells activated under Th17 polarizing conditions in the presence of melatonin (2 ng/ml) and control or IL-2 blocking antibodies. Data are representative of two independent experiments (means and SEM). *p<0.05 of unpaired t test. (C) Immunoblot analysis of the expression of MTNR1A in naive CD4+ T cells activated under Th17 or Tr1 polarizing conditions for 3 days in the presence of melatonin (2 ng/ml). Data are representative of two independent experiments (means and SEM). (D) RT-PCR analysis of rora expression in different CD4+ T cell subsets following in vitro differentiation for 3 days. Data are representative of five independent experiments (means and SEM) *p<0.05 of unpaired t test. (E) Luciferase activity in HEK293 cells cotransfected with a construct coding for RORa and a luciferase reporter construct for the RORa responsive bmal promoter. Data are representative of two independent experiments (means and SEM)*p<0.05 of unpaired t test. (F) IL17 and IL-10 in supernatants of murine CD4+ T cells activated under Th0 or Th17 polarizing conditions in the presence of vehicle, melatonin (2 ng/ml) and ramelteon (10 ng/ml). (G) RT-PCR analysis of rorc and il1 7 expression in CD4+ T cells activated as in (F). Data are representative of two independent experiments (means and SEM) *p<0.05 of unpaired t test. (H and I) Percentage of Phospho/Total Erk ratio (H) and MFI ratio (I) of flow cytometry analysis of Erk1/2 phosphorylation in wild-type or MTNR1A KO CD4+ T cells activated under Th17 polarizing conditions and treated with vehicle, melatonin (2 ng/ml) or agomelatine (20 ng/ml). Data are representative of two independent experiments (means and SEM) *$p<0.05$ of unpaired t test.

IFNγ and IL-2 have been shown to limit Th17 cell differentiation (Kom et al., 2009). However, in our studies Th17 cells were differentiated in the presence of IFNγ-blocking antibodies, and IL-2 blocking antibodies failed to abrogate the suppression of Th17 differentiation by melatonin (FIG. 10a,b). Thus, melatonin suppresses Th17 cell differentiation through a mechanism independent of IFNγ or IL-2.

Physiological concentrations of melatonin result in the activation of signaling pathways controlled by membrane and nuclear receptors (Brzezinski, 1997). The melatonin membrane receptor MTNR1A is expressed by a variety of tissues including cells of the immune system (Jockers et al., 2008; Pozo et al., 1997). In addition, melatonin binds to the nuclear retinoid-related orphan receptor alpha (ROR-α), which is also expressed by immune cells (Pozo et al., 2004) and plays a role in Th17 development (Yang et al., 2008). We detected the expression of both MTNR1A and ROR-α on Th17 cells (FIG. 10c,d). To study the role of MTNR1A signaling on the effects of melatonin on Th17 cells, we used the MTNR1A-specific agonists agomelatine and ramelteon (Karim et al., 2006) (FIG. 10e). Similar to our observations with melatonin, MTNR1A activation by agomelatine or ramelteon suppressed the differentiation of Th17 cells (FIG. 4c,d and FIG. 10f,g). Conversely, melatonin failed to suppress the differentiation of MTNR1A-deficient (MTNR1A KO) Th17 cells used (FIG. 4e,f). Thus, MTNR1A mediates the suppressive effects of melatonin on Th17 cell differentiation.

Example 5. Melatonin Suppresses Th17 Cell Differentiation Via Erk1/2 and C/EBPα Activation REV-ERBα (encoded by nr1d1) is a component of the circadian clock that promotes Th17 differentiation by limiting the expression of NFIL3, a direct inhibitor of rorc transcription (Yu et al., 2013). Melatonin regulates the activity of both circadian and seasonal clocks (Pévet, 2003). Indeed, melatonin levels show a circadian inverse correlation with nr1d1 expression, suggesting that melatonin affects REV-ERBα expression (Kojetin and Burris, 2014). Thus, we investigated whether melatonin acts on REV-ERBα to suppress Th17 cell differentiation.

Using reverse protein arrays (Farez et al., 2009) we analyzed signaling pathways triggered by melatonin in T cells and detected an MTNR1A-dependent increase in the activation of Erk1/2 (FIG. 4g,h; FIG. 10h,i). Of note, Erk1/2 inhibition has been previously shown to enhance Th17 cell differentiation (Tan and Lam, 2010) and Erk1/2 phosphorylation has been linked to the reduced expression of REV-ERB proteins (Castellano et al., 2014; Kojetin and Burris, 2014), but the mechanism involved and its relevance for T cells has not been characterized yet. Through a bioinformatic analysis of the nr1d1 promoter we identified a binding site for the CAAT/enhancer-binding protein a (C/EBPα), a leucine zipper transcription factor involved in the regulation of cellular differentiation (Lekstrom-Himes and Xanthopoulos, 1998). C/EBPα is a downstream target of Erk1/2 activated by phosphorylation (Johnson, 2005). Thus, we analyzed whether Erk1/2 regulates the transcriptional activity of the nr1d1 promoter in a C/EBPα dependent manner.

Th17 cell differentiation in the presence of melatonin led to C/EBPα phosphorylation and the recruitment of C/EBPα to the nr1d1 promoter (FIG. 4i,j). C/EBPα phosphorylation and recruitment to the nr1d1 promoter were suppressed in MTNR1A KO T cells and in the presence of the Erk1/2 inhibitor UO216 (FIG. 4i,j). Hence, melatonin triggers the recruitment of C/EBPα to the nr1d1 promoter in an MTNR1A- and Erk1/2-dependent manner.

To analyze the effects of C/EBPα on the transcriptional activity of the nr1d1 promoter we used a reporter construct in which the nr1d1 promoter controls luciferase expression. Treatment of nr1d1 reporter-transfected HEK293 cells with melatonin or agomelatine resulted in decreased luciferase activity and similar effects were achieved by C/EBPα overexpression (FIG. 4k). Finally, to investigate the role of C/EBPα on the suppression of Th17 cell differentiation by melatonin we used C/EBPα deficient T cells (Yang et al., 2005). C/EBPα-deficiency abrogated the decrease in nr1d1 expression and the suppression of Th17 differentiation induced by melatonin (FIG. 4l,m). Thus, melatonin suppresses the differentiation of Th17 through a mechanism mediated by MTNR1A, Erk1/2 and C/EBPα.

Figure 12:
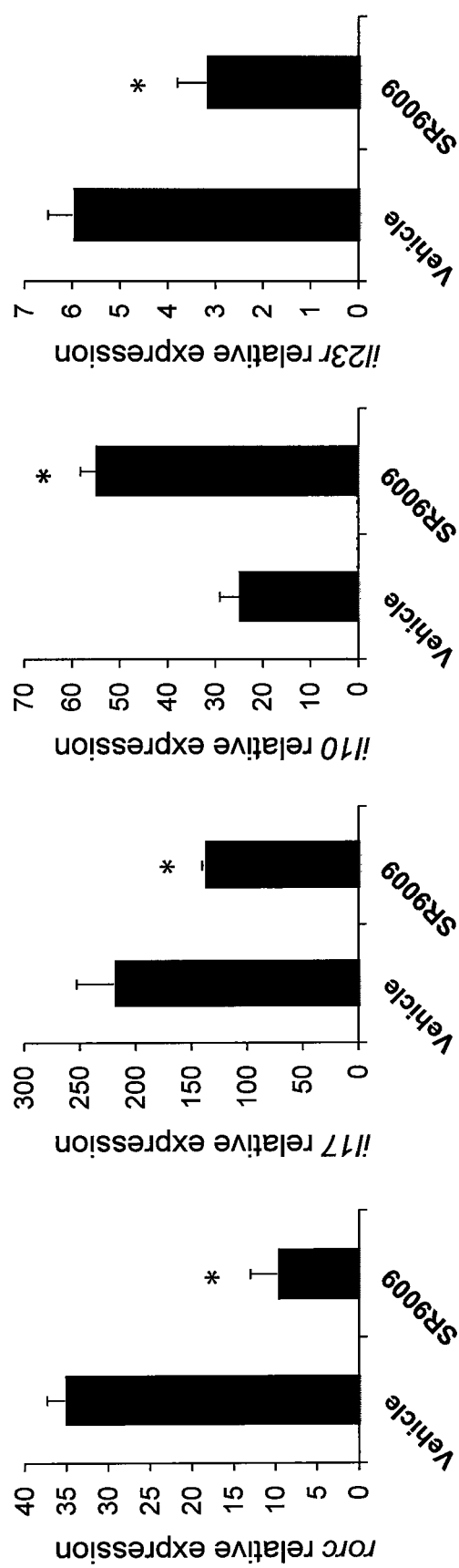
FIG. 12. CD4+ naive T cells were differentiated into Th17 cells by the addition of TFG-b, IL-6 (0 hr), and IL-23 (48 hr) in the presence or absence of the REV-ERB alpha agonist SR9009 (5 micromolar) and analyzed by RT-PCR after 72 hr. *$p<0.05$ of unpaired t test.

In addition, CD4+ naive T cells were differentiated into Th17 cells by the addition of TFG-b, IL-6 (0 hr), and IL-23 (48 hr) in the presence or absence of the REV-ERB alpha agonist SR9009 (5 micromolar) and analyzed by RT-PCR after 72 hr. *p<0.05 of unpaired t test. The results, shown in FIG. 12, show that the REV-ERB agonist suppresses differentiation into Th17 cells.

Example 6. Melatonin Inhibits ROR-γt and ROR-α Expression in Th17 Cells by Inducing Nfil3

Figure 5:
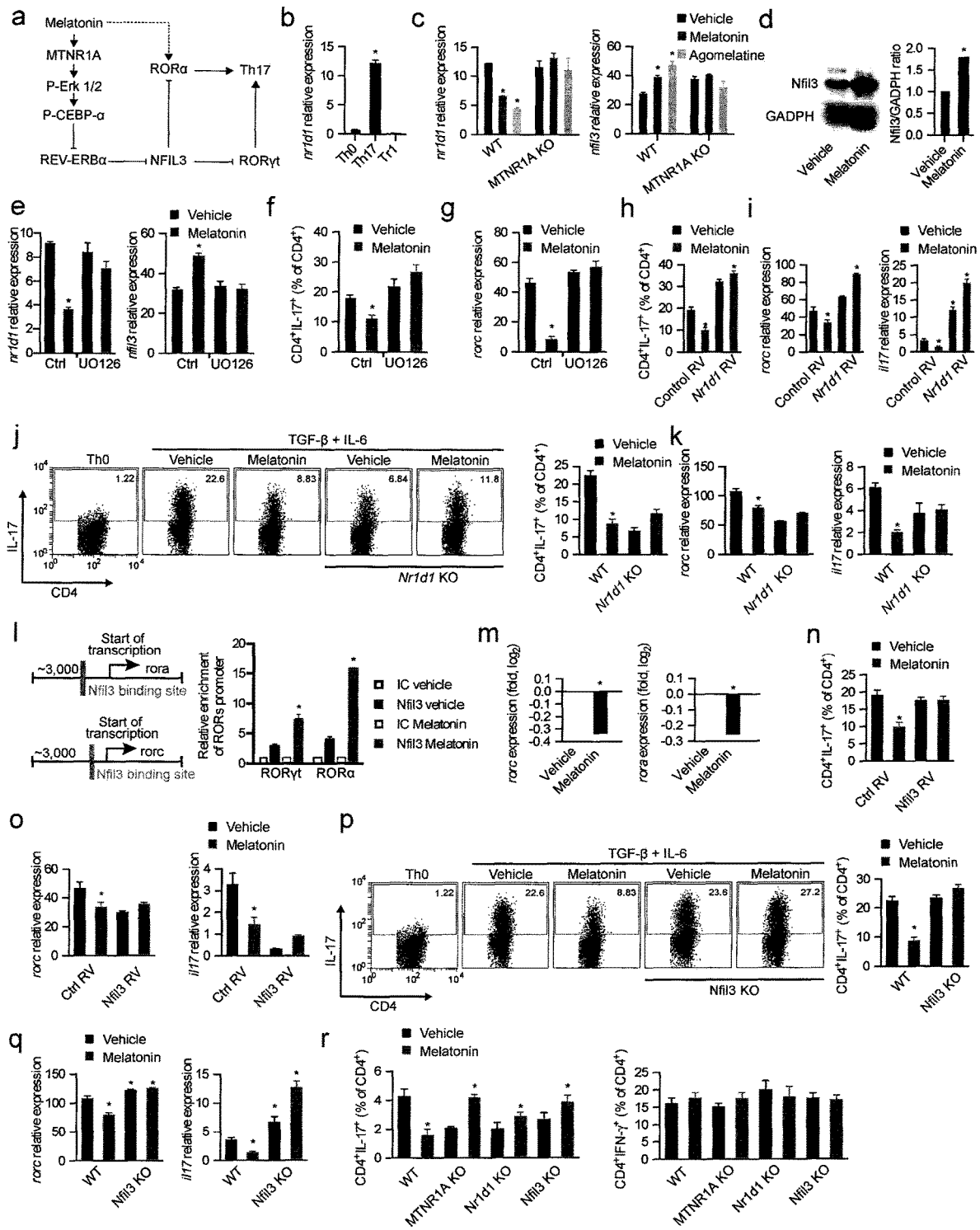
FIG. 5. Melatonin interferes with Th17 cell differentiation by limiting NFIL3 expression. (a) Schematic diagram of the proposed mechanisms mediating the effects of melatonin on Th17 cell differentiation. (b) RT-PCR analysis of nr1d1 expression in CD4+ T cells activated under Th0, Th17 and Tr1 polarizing conditions for 3 days. Data are representative of three independent experiments (means and s.e.m.). * P<0.05 of unpaired T-test. (c) RT-PCR analysis of nr1d1 (left panel) and nfil3 (right panel) expression in CD4+ T cells activated under Th17 polarizing conditions for 3 days treated with vehicle, melatonin (2 ng/ml) or agomelatine 20 ng/ml). Data are representative of three independent experiments (means and s.e.m.). * P<0.05 of unpaired T-test. NFIL3 expression was further confirmed by western blot (d) Data are representative of two independent experiments (means and s.e.m.). (e) RT-PCR analysis of nfil3 expression in CD4+ T cells activated under Th17 polarizing conditions for 3 days in the presence of melatonin (2 ng/ml) and/or UO126. Data are representative of five independent experiments (means and s.e.m.). * P<0.05 of one-way ANOVA. (f,g) Flow cytometry analysis of IL-17 expression (f) and rorc expression (g) in CD4+ T cells activated under Th17 polarizing conditions in the presence of melatonin (2 ng/ml) and/or U0126. Data are representative of three independent experiments (means and s.e.m.) * P<0.05 of one-way ANOVA. (h,i) Flow cytometry analysis of IL-17 expression (h) and rorc and il17 expression (i) in CD4+ T cells activated under Th17 polarizing conditions in the presence of melatonin (2 ng/ml), following infecting with a control or an nr1d1-encoding retrovirus. Data are representative of three independent experiments (means and s.e.m.) * P<0.05 of one-way ANOVA. (j,k) Flow cytometry analysis of IL-17 expression (j) and rorc and il17 expression (k)) in wild type and REV-ERBα deficient CD4+ T cells activated under Th17 polarizing conditions in the presence of melatonin (2 ng/ml). Data are representative of three independent experiments (means and s.e.m.) * P<0.05 of one-way ANOVA. (l) Putative binding sites of Nfil3 in rorc and rora (left panel); ChIP analysis of the interaction of NFIL3 with its putative binding sites in CD4+ T cells activated under Th17 polarizing conditions (right panel). Data are representative of three independent experiments (means and s.e.m.) * P<0.05 of one-way ANOVA. (m) RT-PCR analysis of rorc and rora expression in CD4+ T cells activated under Th17 polarizing conditions in the presence of melatonin (2 ng/ml). Data are representative of three independent experiments (means and s.e.m.) * P<0.05 of unpaired T-test. (n,o) Flow cytometry analysis of IL-17 expression (n) and rorc and il17 expression (o) in CD4+ T cells activated under Th17 polarizing conditions in the presence of melatonin (2 ng/ml) and transduced with a control or nfil3-encoding retrovirus. Data are representative of three independent experiments (means and s.e.m.) * P<0.05 of one-way ANOVA. (p,q) Flow cytometry analysis of IL-17 expression (p) and rorc and il17 expression (q) in wild type mice and NFIL3-deficient in CD4+ T cells activated under Th17 polarizing conditions in the presence of melatonin (2 ng/ml). Data are representative of three independent experiments (means and s.e.m.) * P<0.05 of one-way ANOVA. (r) Flow cytometry analysis of IL-17 and IFN-γ expression in CD4+ T cells from RAG-1 deficient mice reconstituted with wild type, MTNR1A-REV-ERBα or NFIL3-deficient CD4+ T cells, immunized with MOG$_{35-55}$ in CFA and treated with vehicle or melatonin (5 mg/kg). * P<0.05 of unpaired T-test. See also FIG. 11

NFIL3 limits Th17 cell differentiation by suppressing the expression of ROR-γt (Yu et al., 2013). REV-ERBα inhibits nfil3 expression (Yu et al., 2013). Thus, we hypothesized that the decrease in nr1d1 expression induced by melatonin results in the NFIL3-dependent inhibition of rorc expression (FIG. 5a). We detected nr1d1 expression in Th17 cells, but not in Th0 or Tr1 cells (FIG. 5b). Melatonin suppressed nr1d1 expression during Th17 cell differentiation, resulting in a concomitant increase in the expression of the ROR-γt repressor NFIL3 (FIG. 5c,d). In agreement with our results on Th17 cell differentiation, the regulation of REV-ERBα and NFIL3 expression by melatonin was mediated by its membrane receptor MTNR1A and Erk1/2 (FIGS. 5c-g). The relevance of the regulation of REV-ERBα expression for the modulation of Th17 cell differentiation by melatonin was confirmed in nr1d1 overexpression experiments and by the use of REV-ERBα deficient T cells. Nr1d1 overexpression and REV-ERBα deficiency abrogated the effects of melatonin on Th17 cell differentiation (FIGS. 5h-k). Hence, MTNR1A-dependent signaling triggered by melatonin suppresses Th17 cell differentiation through the regulation of REV-ERBα expression.

ROR-α promotes Th17 cell differentiation (Yang et al., 2008). Accordingly, ROR-α activation by the specific agonist CGP 52608 boosted Th17 cell differentiation (FIG. 4c,d). ROR-α is directly activated by melatonin (Brzezinski, 1997). Indeed, melatonin boosted the differentiation of MTNR1A-deficient Th17 cells (FIG. 4e), suggesting that melatonin-triggered MTNR1A signaling interferes with the promotion of Th17 cell differentiation by ROR-α. Based on the inhibitory effects of NFIL3 on ROR-γt expression and Th17 cell differentiation (Yu et al., 2013), we studied whether NFIL3 also inhibits ROR-α expression.

Figure 11:
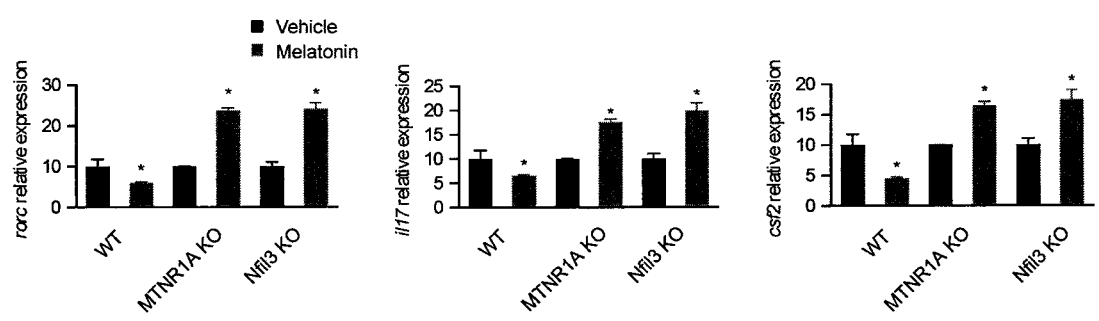
FIG. 11. Melatonin Effect in EAE Is Mediated by MTNR1A and Nfil3 in CD4+ T Cells, Related to FIG. 5. RT-PCR analysis of rorc, il17 and csf2 expression in CD4+ T cells from the CNS of RAG-1-deficient mice reconstituted with wild-type, MTNR1A- or NFIL3-deficient CD4+ T cells, immunized with MOG35-55 in CFA and treated with vehicle or melatonin (5 mg/kg). *$p<0.05$ of unpaired t test.

A bioinformatics analysis identified NFIL3 binding sites in the rora and rorc promoters. Accordingly, we detected the recruitment of NFIL3 to the rora and rorc promoters in CD4+ T cells activated under Th17 polarizing conditions in the presence of melatonin, concomitant with a reduced expression of both ROR-α and ROR-γt (FIGS. 5l,m). We then investigated the relevance of the regulation of NFIL3 expression for the modulation of Th17 cell differentiation. Overexpression of NFIL3 (FIGS. 5n,o) and NFIL3-deficiency (FIGS. 5p,q) abrogated the suppressive effects of melatonin on Th17 cell differentiation. Thus, the regulation of NFIL3 expression by melatonin mediates its inhibitory effects on the differentiation of Th17 cells in vitro. To evaluate the role of MTNR1A and NFIL3 on the suppression of Th17 cell differentiation by melatonin in vivo we used RAG-1 deficient mice reconstituted with wild type, MTNR1A, REV-ERBα or NFIL3-deficient CD4+ T cells and immunized with MOG$_{35-55}$ in CFA. In agreement with our in vitro observations, the suppression of Th17 cell differentiation by melatonin in vivo was abrogated by MTNR1A, REV-ERBα and NFIL3-deficiency (FIG. 5r, FIG. 11). Indeed, we detected increased Th17 cell differentiation in response to treatment of mice reconstituted with MTNR1A-, REV-ERBα or NFIL3-deficient T cells, most likely reflecting the unopposed agonistic activity of melatonin on ROR-α and its promoting effects on the differentiation of Th17 cells. Taken together, these data suggest that melatonin interferes with Th17 cell differentiation via the inhibition of ROR-γt and ROR-α expression through an NFIL3-dependent mechanism.

Example 7. Melatonin Boosts Tr1 Cell Differentiation Via Erk1/2 and ROR-α

Figure 2:
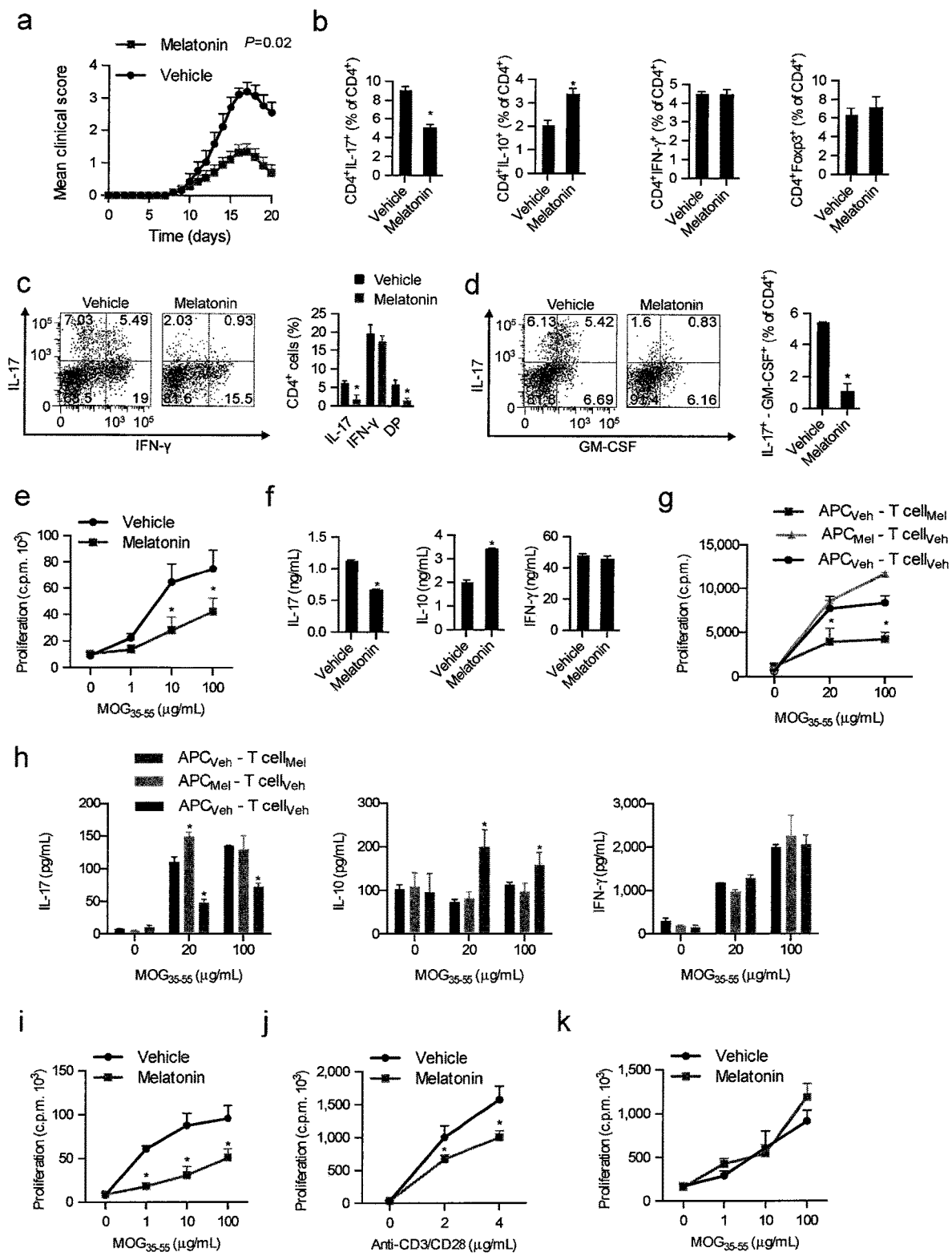
FIG. 2. Melatonin administration ameliorates EAE. (a) EAE development in C57/B6 treated with vehicle (0.01% DMSO) or melatonin (5 mg/kg). Data are representative of three independent experiments (means and s.e.m.) (n≥20 mice/group). P value corresponds for the effect of treatment in a repeated measures mixed effect model. (b) Flow cytometry analysis of IL-17$^+$, IL10$^+$, IFN-$\gamma^+$ and FoxP3$^+$ CD4$^+$ cells from the spleen of vehicle or melatonin treated mice at day 7 after disease induction. At least 4 mice were analyzed per group and data is presented as mean±SEM. * P<0.05 of unpaired T-test. (c-d) Flow cytometry analysis of IL-17$^+$, IFN-$\gamma^+$, IL-17$^+$-IFN-$\gamma^+$ (DP) and IL-17$^+$-GM-CSF$^+$ CD4$^+$ T cells from the CNS of control- or melatonin-treated mice at the clinical peak of EAE * P<0.05 of unpaired T-test. (e) Proliferative responses of CD4$^+$ T cells to MOG$_{35\text{-}55}$ of vehicle or melatonin treated mice. At least 3 mice were analyzed per group and data is presented as mean±s.e.m. * P<0.05 of one-way ANOVA. (f) Cytokine secretion by proliferating CD4$^+$ T cells from vehicle and melatonin treated. Data are representative of three independent experiments (means and s.e.m.)* P<0.05 of unpaired T-test. (g) Proliferative responses and cytokine profile (h) of CD4$^+$ T cells in co-culture with dendritic cells derived from melatonin-treated or untreated mice. Data are representative of three independent experiments (means and s.e.m.). * P<0.05 of one-way ANOVA. (i) Proliferative responses of melatonin treated 2D2 CD4$^+$ T cells to MOG$_{35\text{-}55}$ in the presence of dendritic cells. Data are representative of three independent experiments (means and s.e.m.)* P<0.05 of one-way ANOVA. (j) Proliferative responses of melatonin treated 2D2 CD4$^+$ T cells to MOG$_{35\text{-}55}$ stimulated only with anti-CD3 and anti-CD28. Data are representative of three independent experiments (means and s.e.m.)* P<0.05 of one-way ANOVA. (k) Proliferative responses of treated 2D2 CD4$^+$ T cells to MOG$_{35\text{-}55}$ stimulated melatonin-treated DCs. Data are representative of three independent experiments (means and s.e.m.). See also FIG. 7a-e FIG. 3. Melatonin interferes with human Th17 cell differentiation and boosts Tr1 generation. (a) Flow cytometry analysis of IL-17 expression in human Th17 differentiated CD4$^+$ T cells (IL-1β, IL-6 and TGF-β1) in the presence or absence of melatonin (500 ng/ml) and agomelatine (500 ng/ml). Data are representative of three independent experiments (means and s.e.m.) * P<0.05 of one-way ANOVA. (b). Cytokine quantification by ELISA of IL-17 in human Th17 differentiated CD4$^+$ T cells in the presence or absence of melatonin (500 ng/ml) and agomelatine (500 ng/ml). Data are representative of three independent experiments (means and s.e.m.) * P<0.05 of one-way ANOVA. (c) RT-PCR analysis of Th17 cells cultured as in a. Data are representative of three independent experiments (means and s.e.m.) * P<0.05 of one-way ANOVA. (d) Flow cytometry analysis of IFN-g expression in human Th1-differentiated CD4+ T cells (IL-12) in the presence or absence of melatonin (500 ng/ml) and agomelatine (500 ng/ml). Data are representative of three independent experiments (means and SEM). (e). Cytokine quantification by ELISA of IFN-$\gamma$ in human Th1 differentiated CD4$^+$ T cells in the presence or absence of melatonin (500 ng/ml) and agomelatin (500 ng/ml). Data are representative of three independent experiments (means and s.e.m.) * P<0.05 of one-way ANOVA. (f) RT-PCR analysis of Th1 cells cultured as in d. Data are representative of three independent experiments (means and s.e.m.) * P<0.05 of one-way ANOVA. (g) Flow cytometry analysis of IL-10 expression in human Tr1 differentiated CD4+ T cell in the presence or absence of melatonin (500 ng/ml) and agomelatin (500 ng/ml). Data are representative of three independent experiments (means and s.e.m.) * P<0.05 of one-way ANOVA. (h) Quantitative PCR analysis of Tr1 cells cultured as in f. Data are representative of three independent experiments (means and s.e.m.). * P<0.05 of one-way ANOVA. See also FIG. 8
Figure 6:
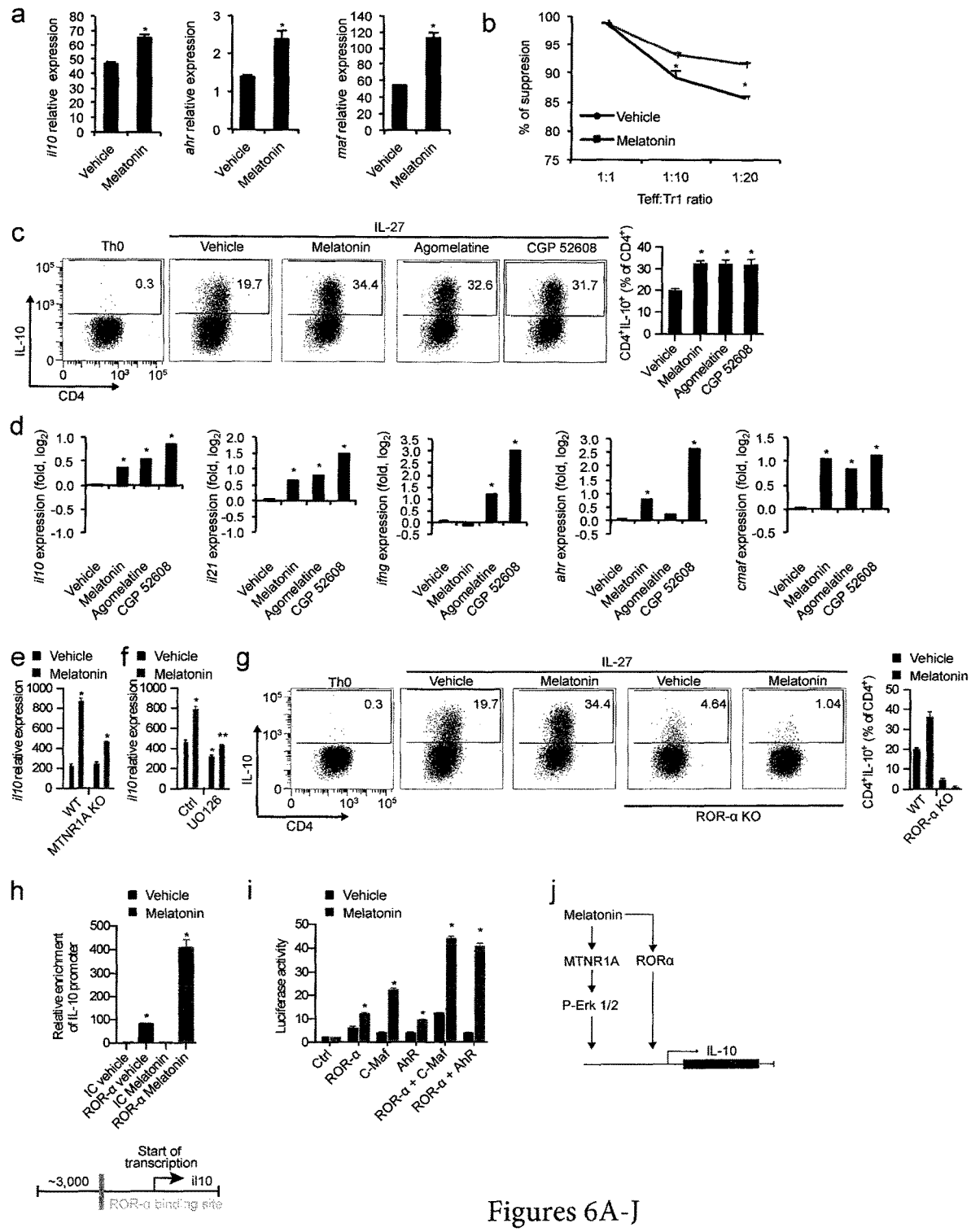
FIG. 6. Melatonin boosts Tr1 cell differentiation. (a) RT-PCR analysis of il1 0, ahr and maf expression in Tr1 differentiated CD4+ T cells in the presence or absence of melatonin (2 ng/ml). Data are representative of three independent experiments (means and s.e.m.). * P<0.05 of one-way ANOVA (b) In vitro suppression assay, treated or untreated differentiated Tr1 cells as in a, were co-cultured after 72 hs with CD4+ T cells previously labeled with CSFE, and proliferation cycles (CSFE dilution) were measured after 48 hs by flow cytometry. Data are representative of two independent experiments (means and s.e.m.) * P<0.05 of one-way ANOVA. (c) Flow cytometry analysis of IL-10 expression in Tr1 differentiated CD4+ T cells in the presence or absence of melatonin (2 ng/ml), agomelatine (20 ng/ml, MTNR1A ligand) and CGP 52608 (20 ng/ml, ROR-α ligand). Data are representative of three independent experiments (means and s.e.m.) * P<0.05 of one-way ANOVA. (d) RT-PCR analysis of Tr1 cells cultured as in c. Data are representative of three independent experiments (means and s.e.m.) * P<0.05 of one-way ANOVA. (e) RT-PCR analysis of il10 expression as in c, in wild type mice and MTNR1A deficient mice. Data are representative of three independent experiments (means and s.e.m.) * P<0.05 of one-way ANOVA. (f) RT-PCR expression of il10 in melatonin treated Tr1 cells with or without the addition of UO126. Data are representative of five independent experiments (means and s.e.m.). * P<0.05 of unpaired T-test vs vehicle and signaling inhibitor control condition. ** P<0.05 vs vehicle of UO126-treated condition. (g) Flow cytometry analysis of IL-10 expression as in c, in wild type mice and ROR-α deficient mice. (h) ROR-α putative binding site present in the il10 promoter (lower panel), and chromatin immunoprecipitation with anti-ROR-α (upper panel) Data are representative of three independent experiments (means and s.e.m.). * P<0.05 of unpaired T-test. (i) Luciferase activity of HEK-293 cells transfected with a luciferase reporter construct for the il10 promoter. Data are representative of three independent experiments (means and s.e.m.)* P<0.05 of unpaired T-test. (j) Schematic diagram depicting the effects of melatonin in Tr1 cells.

CD4+ IL-10 producing Tr1 cells play an important role in the regulation of the immune response (Pot et al., 2011; Roncarolo et al., 2006). The amelioration of EAE by melatonin administration was associated with an increase in IL-10 producing T cells (FIG. 2). Thus, we investigated the effects of melatonin on the activation of naïve CD4+ T cells under Tr1 polarizing conditions. We found that melatonin boosted the expression of IL-10 and the Tr1-associated molecules il21, ahr and cmaf (Apetoh et al., 2010) (FIG. 6a). In addition, melatonin boosted the suppressive activity of Tr1 cells in vitro (FIG. 6b).

We then investigated the mechanisms underlying the effects of melatonin on Tr1 regulatory cells. We detected the expression of both MTNR1A and ROR-α by Tr1 cells (FIGS. 10c,d). Indeed, both agomelatine and CGP 52608, specific agonist for MTNR1A and ROR-α, respectively, boosted Tr1 cell differentiation (FIGS. 6c,d). In agreement with these results, MTNR1A deficiency or inhibition of MTNR1A-activated Erk1/2 by UO126 interfered with the boost in Tr1 differentiation by melatonin (FIGS. 6e,f). Of note, Erk1/2 activation is reported to promote cmaf-dependent IL-10 production by CD4+ T cells (Saraiva et al., 2009). In addition, ROR-α deficiency suppressed the differentiation of Tr1 cells induced by IL-27 and its boost by melatonin (FIG. 6g).

ROR-α exerts its biological effects by binding to ROR response elements (ROREs) in target genes (Jetten, 2009). A bioinformatic analysis identified ROR-α binding sites in the il10 promoter (FIG. 6h), suggesting that melatonin may increase the recruitment of ROR-α to the il10 promoter and consequently, il10 transcription. In agreement with this hypothesis, we detected increased binding of ROR-α to the il10 promoter following T-cell activation under Tr1 polarizing conditions in the presence of melatonin (FIG. 6h). Moreover, ROR-α transactivated the il10 promoter in reporter assays, and synergized with the aryl hydrocarbon receptor (AhR) and c-Maf to boost their ability to promote il10 expression agregar paper ivan (Apetoh et al., 2010; Gandhi et al., 2010) (FIG. 6i). Taken together, these data suggest that melatonin boosts Tr1 cell differentiation through its effects on MTNR1A and ROR-α (FIG. 6j).

REFERENCES

Apetoh, L., Quintana, F. J., Pot, C., Joller, N., Xiao, S., Kumar, D., Burns, E. J., Sherr, D. H., Weiner, H. L., and Kuchroo, V. K. (2010). The aryl hydrocarbon receptor interacts with c-Maf to promote the differentiation of type 1 regulatory T cells induced by IL-27. Nat. Immunol. 11, 854-861.

Ascherio, A., Munger, K. L., Lennette, E. T., Spiegelman, D., Hernan, M. A., Olek, M. J., Hankinson, S. E., and Hunter, D. J. (2001). Epstein-Barr virus antibodies and risk of multiple sclerosis: a prospective study. Jama 286, 3083-3088.

Ascherio, A., Munger, K. L., and Liinemann, J. D. (2012). The initiation and prevention of multiple sclerosis. Nature Reviews Neurology 8, 602-612.

Ascherio, A., Munger, K. L., and Simon, K. C. (2010). Vitamin D and multiple sclerosis. The Lancet Neurology 9, 599-612.

Ascherio, A., Munger, K. L., White, R., Köchert, K., Simon, K. C., Polman, C. H., Freedman, M. S., Hartung, H.-P., Miller, D. H., Montalban, X., et al. (2014). Vitamin D as an Early Predictor of Multiple Sclerosis Activity and Progression. JAMA Neurol 71, 306.

Astier, A. L., Meiffren, G., Freeman, S., and Hafler, D. A. (2006). Alterations in CD46-mediated Tr1 regulatory T cells in patients with multiple sclerosis. Journal of Clinical Investigation 116, 3252-3257.

Beecham, A. H., Patsopoulos, N. A., Xifara, D. K., Davis, M. F., Kemppinen, A., Cotsapas, C., Shah, T. S., Spencer, C., Booth, D., Goris, A., et al. (2013). Analysis of immune-related loci identifies 48 new susceptibility variants for multiple sclerosis. Nat Genet 45, 1353-1360.

Brzezinski, A. (1997). Melatonin in humans. N Engl J Med 336, 186-195.

Castellano, I., Ercolesi, E., and Palumbo, A. (2014). Nitric Oxide Affects ERK Signaling through Down-Regulation of MAP Kinase Phosphatase Levels during Larval Development of the Ascidian Ciona intestinalis. PLoS ONE 9, e102907.

Codarri, L., Gyülvészi, G., Tosevski, V., Hesske, L., Fontana, A., Magnenat, L., Suter, T., and Becher, B. (2011). RORγt drives production of the cytokine GM-CSF in helper T cells, which is essential for the effector phase of autoimmune neuroinflammation. Nat. Immunol. 12, 560-567.

Correale, J., Ysrraelit, M. C., and Gaitan, M. I. (2009). Immunomodulatory effects of Vitamin D in multiple sclerosis. Brain 132, 1146-1160.

Correale, J., and Farez, M. (2007). Association between parasite infection and immune responses in multiple sclerosis. Ann. Neurol. 61, 97-108.

Correale, J., Fiol, M., and Gilmore, W. (2006). The risk of relapses in multiple sclerosis during systemic infections. Neurology 67, 652-659.

Dominique L. P. Baeten, and Kuchroo, V. K. (2013). Interleukin-17 and a tale of two autoimmune diseases. Nature Medicine 19, 824-825.

El-Behi, M., Ciric, B., Dai, H., Yan, Y., Cullimore, M., Safavi, F., Zhang, G.-X., Dittel, B. N., and Rostami, A. (2011). The encephalitogenicity of T. Nat. Immunol. 12, 568-575.

Farez, M. F., Fiol, M. P., Gaitan, M. I., Quintana, F. J., and Correale, J. (2014). Sodium intake is associated with increased disease activity in multiple sclerosis. Journal of Neurology, Neurosurgery & Psychiatry.

Farez, M. F., Quintana, F. J., Gandhi, R., Izquierdo, G., Lucas, M., and Weiner, H. L. (2009). Toll-like receptor 2 and poly(ADP-ribose) polymerase 1 promote central nervous system neuroinflammation in progressive EAE. Nat. Immunol. 10, 958-964.

Fassi, J., Russo Picasso, M. F., Furci, A., Sorroche, P., Jáuregui, R., and Plantalech, L. (2003). [Seasonal variations in 25-hydroxyvitamin D in young and elderly and populations in Buenos Aires City]. Medicina (B Aires) 63, 215-220.

Gandhi, R., Kumar, D., Burns, E. J., Nadeau, M., Dake, B., Laroni, A., Kozoriz, D., Weiner, H. L., and Quintana, F. J. (2010). Activation of the aryl hydrocarbon receptor induces human type 1 regulatory T cell-like and Foxp3(+) regulatory T cells. Nat. Immunol. 11, 846-853.

Graham, C., Cook, M. R., Kavet, R., Sastre, A., and Smith, D. K. (1998). Prediction of nocturnal plasma melatonin from morning urinary measures. J Pineal Res 24, 230-238.

Hedström, A. K., Åkerstedt, T., Hillert, J., Olsson, T., and Alfredsson, L. (2011). Shift work at young age is associated with increased risk for multiple sclerosis. Ann. Neurol. 70, 733-741.

Hernan, M. A. (2005). Cigarette smoking and the progression of multiple sclerosis. Brain 128, 1461-1465.

Hickie, I. B., and Rogers, N. L. (2011). Novel melatonin-based therapies: potential advances in the treatment of major depression. Lancet 378, 621-631.

Jetten, A. M. (2009). Retinoid-related orphan receptors (RORs): critical roles in development, immunity, circadian rhythm, and cellular metabolism. Nucl Recept Signal 7, e003.

Jin, Y., de Pedro-Cuesta, J., Söderström, M., Stawiarz, L., and Link, H. (2000). Seasonal patterns in optic neuritis and multiple sclerosis: a meta-analysis. Journal of the Neurological Sciences 181, 56-64.

Jockers, R., Maurice, P., Boutin, J. A., and Delagrange, P. (2008). Melatonin receptors, heterodimerization, signal transduction and binding sites: what's new? British Journal of Pharmacology 154, 1182-1195.

Johnson, P. F. (2005). Molecular stop signs: regulation of cell-cycle arrest by C/EBP transcription factors. J. Cell. Sci. 118, 2545-2555.

Karim, A., Tolbert, D., and Cao, C. (2006). Disposition kinetics and tolerance of escalating single doses of ramelteon, a high-affinity MT1 and MT2 melatonin receptor agonist indicated for treatment of insomnia. J Clin Pharmacol 46, 140-148.

Kobayashi, T., Steinbach, E. C., Russo, S. M., Matsuoka, K., Nochi, T., Maharshak, N., Borst, L. B., Hostager, B., Garcia-Martinez, J. V., Rothman, P. B., et al. (2014). NFIL3-deficient mice develop microbiota-dependent, IL-12/23-driven spontaneous colitis. The Journal of Immunology 192, 1918-1927.

Kojetin, D. J., and Burris, T. P. (2014). REV-ERB and ROR nuclear receptors as drug targets. Nat Rev Drug Discov 13, 197-216.

Korn, T., Bettelli, E., Oukka, M., and Kuchroo, V. K. (2009). IL-17 and Th17 Cells. Annu. Rev. Immunol. 27, 485-517.

Lathrop, S. K., Bloom, S. M., Rao, S. M., Nutsch, K., Lio, C.-W., Santacruz, N., Peterson, D. A., Stappenbeck, T. S., and Hsieh, C.-S. (2011). Peripheral education of the immune system by colonic commensal microbiota. Nature 478, 250-254.

Lee, Y., Awasthi, A., Yosef, N., Quintana, F. J., Xiao, S., Peters, A., Wu, C., Kleinewietfeld, M., Kunder, S., Hafler, D. A., et al. (2012a). Induction and molecular signature of pathogenic TH17 cells. Nat. Immunol. 1-11.

Lee, Y., Awasthi, A., Yosef, N., Quintana, F. J., Xiao, S., Peters, A., Wu, C., Kleinewietfeld, M., Kunder, S., Hafler, D. A., et al. (2012b). Induction and molecular signature of pathogenic TH17 cells. Nat. Immunol. 13, 991-999.

Lekstrom-Himes, J., and Xanthopoulos, K. G. (1998). Biological role of the CCAAT/enhancer-binding protein family of transcription factors. J. Biol. Chem. 273, 28545-28548.

Løken-Amsrud, K. I., Holmoy, T., Bakke, S. J., Beiske, A. G., Bjerve, K. S., Bjørnarå, B. T., Hovdal, H., Lilleis, F., Midgard, R., Pedersen, T., et al. (2012). Vitamin D and disease activity in multiple sclerosis before and during interferon-β treatment. Neurology 79, 267-273.

Macchi, M. M., and Bruce, J. N. (2004). Human pineal physiology and functional significance of melatonin. Front Neuroendocrinol 25, 177-195.

McGeachy, M. J., Bak-Jensen, K. S., Chen, Y., Tato, C. M., Blumenschein, W., McClanahan, T., and Cua, D. J. (2007). TGF-β and IL-6 drive the production of IL-17 and IL-10 by T cells and restrain TH-17 cell-mediated pathology. Nat. Immunol. 8, 1390-1397.

McMullan, C. J., Schernhammer, E. S., Rimm, E. B., Hu, F. B., and Forman, J. P. (2013). Melatonin secretion and the incidence of type 2 diabetes. Jama 309, 1388-1396.

Miossec, P., Korn, T., and Kuchroo, V. K. (2009). Interleukin-17 and type 17 helper T cells. N Engl J Med 361, 888-898.

Morera, A. L., and Abreu, P. (2007). Daytime/night-time and summer/winter melatonin and malondialdehyde rhythms: an inverse relationship. J Pineal Res 43, 313-314.

Pévet, P. (2003). Melatonin: from seasonal to circadian signal. J. Neuroendocrinol. 15, 422-426.

Polman, C. H., Reingold, S. C., Banwell, B., Clanet, M., Cohen, J. A., Filippi, M., Fujihara, K., Havrdova, E., Hutchinson, M., Kappos, L., et al. (2011). Diagnostic criteria for multiple sclerosis: 2010 Revisions to the McDonald criteria. Ann. Neurol. 69, 292-302.

Pot, C., Apetoh, L., Awasthi, A., and Kuchroo, V. K. (2011). Induction of regulatory Tr1 cells and inhibition of TH17 cells by IL-27. Seminars in Immunology 23, 438-445.

Pozo, D., Delgado, M., Fernandez-Santos, J. M., Calvo, J. R., Gomariz, R. P., Martin-Lacave, I., Ortiz, G. G., and Guerrero, J. M. (1997). Expression of the Mel1a-melatonin receptor mRNA in T and B subsets of lymphocytes from rat thymus and spleen. Faseb J. 11, 466-473.

Pozo, D., Garcia-Maurifio, S., Guerrero, J. M., and Calvo, J. R. (2004). mRNA expression of nuclear receptor RZR/RORalpha, melatonin membrane receptor MT1, and hydroxindole-O-methyltransferase in different populations of human immune cells. J Pineal Res 37, 48-54.

Quintana, F. J., Basso, A. S., Iglesias, A. H., Korn, T., Farez, M. F., Bettelli, E., Caccamo, M., Oukka, M., and Weiner, H. L. (2008). Control of Treg and TH17 cell differentiation by the aryl hydrocarbon receptor. Nature 453, 65-71.

Roncarolo, M.-G., Gregori, S., Battaglia, M., Bacchetta, R., Fleischhauer, K., and Levings, M. K. (2006). Interleukin-10-secreting type 1 regulatory T cells in rodents and humans. Immunol. Rev. 212, 28-50.

Rosecrans, R., and Dohnal, J. C. (2014). Clinical Biochemistry. Clinical Biochemistry 47, 670-672.

Runia, T. F., Hop, W. C. J., de Rijke, Y. B., Buljevac, D., and Hintzen, R. Q. (2012). Lower serum vitamin D levels are associated with a higher relapse risk in multiple sclerosis. Neurology 79, 261-266.

Sakaguchi, S., Miyara, M., Costantino, C. M., and Hafler, D. A. (2010). FOXP3+ regulatory T cells in the human immune system. Nature Reviews Immunology 10, 490-500.

Saraiva, M., and O'Garra, A. (2010). The regulation of IL-10 production by immune cells. Nature Reviews Immunology 10, 170-181.

Saraiva, M., Christensen, J. R., Veldhoen, M., Murphy, T. L., Murphy, K. M., and O'Garra, A. (2009). Interleukin-10 Production by Th1 Cells Requires Interleukin-12-Induced STAT4 Transcription Factor and ERK MAP Kinase Activation by High Antigen Dose. Immunity 31, 209-219.

Sawcer, S., Hellenthal, G., Pirinen, M., Spencer, C. C. A., Patsopoulos, N. A., Moutsianas, L., Dilthey, A., Su, Z., Freeman, C., Hunt, S. E., et al. (2011). Genetic risk and a primary role for cell-mediated immune mechanisms in multiple sclerosis. Nature 476, 214-219.

Schernhammer, E. S., Rosner, B., Willett, W. C., Laden, F., Colditz, G. A., and Hankinson, S. E. (2004). Epidemiology of urinary melatonin in women and its relation to other hormones and night work. Cancer Epidemiol. Biomarkers Prev. 13, 936-943.

Simpson, S., Taylor, B., Blizzard, L., Ponsonby, A.-L., Pittas, F., Tremlett, H., Dwyer, T., Gies, P., and van der Mei, I. (2010). Higher 25-hydroxyvitamin D is associated with lower relapse risk in multiple sclerosis. Ann. Neurol. 68, 193-203.

Sospedra, M., and Martin, R. (2005). Immunology of multiple sclerosis. Annu. Rev. Immunol. 23, 683-747.

Spelman, T., Gray, O., Trojano, M., Petersen, T., Izquierdo, G., Lugaresi, A., Hupperts, R., Bergamaschi, R., Duquette, P., Grammond, P., et al. (2014). Seasonal variation of relapse rate in multiple sclerosis is latitude dependent. Ann. Neurol.

Steinman, L. (2014). Immunology of Relapse and Remission in Multiple Sclerosis. Annu. Rev. Immunol. 32, 257-281.

Tan, A. H. M., and Lam, K. P. (2010). Pharmacologic Inhibition of MEK-ERK Signaling Enhances Th17 Differentiation. The Journal of Immunology 184, 1849-1857.

Ueno-Towatari, T., Norimatsu, K., Blazejczyk, K., Tokura, H., and Morita, T. (2007). Seasonal Variations of Melatonin Secretion in Young Females under Natural and Artificial Light Conditions in Fukuoka, Japan. J Physiol Anthropol 26, 209-215.

Viglietta, V., Baecher-Allan, C., Weiner, H. L., and Hafler, D. A. (2004). Loss of functional suppression by CD4+ CD25+ regulatory T cells in patients with multiple sclerosis. J. Exp. Med. 199, 971-979.

Wu, C., Yosef, N., Thalhamer, T., Zhu, C., Xiao, S., Kishi, Y., Regev, A., and Kuchroo, V. K. (2013). Induction of pathogenic TH17 cells by inducible salt-sensing kinase SGK1. Nature 1-5.

Yang, J., Croniger, C. M., Lekstrom-Himes, J., Zhang, P., Fenyus, M., Tenen, D. G., Darlington, G. J., and Hanson, R. W. (2005). Metabolic response of mice to a postnatal ablation of CCAAT/enhancer-binding protein alpha. J. Biol. Chem. 280, 38689-38699.

Yang, X. O., Pappu, B. P., Nurieva, R., Akimzhanov, A., Kang, H. S., Chung, Y., Ma, L., Shah, B., Panopoulos, A. D., Schluns, K. S., et al. (2008). T Helper 17 Lineage Differentiation Is Programmed by Orphan Nuclear Receptors RORα and RORγ. Immunity 28, 29-39.

Yu, X., Rollins, D., Ruhn, K. A., Stubblefield, J. J., Green, C. B., Kashiwada, M., Rothman, P. B., Takahashi, J. S., and Hooper, L. V. (2013). TH17 cell differentiation is regulated by the circadian clock. Science 342, 727-730.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of reducing seasonal worsening of MS in a subject who has MS, the method comprising:
   identifying a subject who has a history of seasonal worsening of MS;
   detecting a level of melatonin in a sample from the subject;
   comparing the level of melatonin in the sample to a reference level of melatonin;
   identifying the subject as having a level of melatonin below the reference level; and
   administering a therapeutically effective amount of a melatonin agonist to the subject who has a level of melatonin below the reference level.

2. The method of claim 1, wherein the reference level of melatonin is or corresponds to 20, 20.5, 21, 21.5, 22, 22.5, 23, 23.5, or 24 ng/mg creatinine.

3. The method of claim 1, wherein the melatonin agonist is ramelteon ((S)—N-[2-(1,6,7,8-tetrahydro-2H-indeno[5,4-b] furan-8-yl)ethyl]propionamide), agomelatine (N-[2-(7-methoxynaphthalen-1-yl)ethyl]acetamide), tasimelteon ((1R, 2R)—N-[2-(2,3-dihydrobenzofuran-4-yl)cyclopropyl-methyl]propanamide), or TIK-301 (LY-156735) (N-[(2R)-(6-Chloro-5-methoxy-1H-indol-3-yl)propyl]acetamide).

4. The method of claim 1, wherein the subject has one or more symptoms associated with seasonal worsening of their MS, has low melatonin levels, lives in a climate where a low-melatonin season is occurring or about to occur, or lives in a climate where melatonin levels are typically low.

5. The method of claim 1, further comprising administering a REV-ERB agonist or a ROR agonist.

6. The method of claim 1, wherein the melatonin agonist is administered orally, nasally, intravenously, or intrathecally.

7. The method of claim 1, comprising detecting a level of 6-sulfatoxymelatonin (6-SM).

8. A method of decreasing levels of Th17 cells or increasing levels of Tr1 cells in a subject, the method comprising:
   identify a subject who has a history of seasonal worsening of MS;
   detecting a level of melatonin in a sample from the subject;
   comparing the level of melatonin in the sample to a reference level of melatonin;
   identifying the subject as having a level of melatonin below the reference level; and
   administering a therapeutically effective amount of a melatonin agonist to the subject who has a level of melatonin below the reference level.

9. The method of claim 8, wherein the melatonin agonist is ramelteon ((S)—N-[2-(1,6,7,8-tetrahydro-2H-indeno[5,4-b] furan-8-yl)ethyl]propionamide), agomelatine (N-[2-(7-methoxynaphthalen-1-yl)ethyl]acetamide), tasimelteon ((1R, 2R)—N-[2-(2,3-dihydrobenzofuran-4-yl)cyclopropyl-methyl]propanamide), or TIK-301 (LY-156735) (N-[(2R)-(6-Chloro-5-methoxy-1H-indol-3-yl)propyl]acetamide).

10. The method of claim 8, further comprising administering a REV-ERB agonist or a ROR agonist.

11. The method of claim 8, wherein the melatonin agonist is administered orally, nasally, intravenously, or intrathecally.

12. The method of claim 8, comprising detecting a level of 6-sulfatoxymelatonin (6-SM).

\* \* \* \* \*

UNITED STATES PATENT AND TRADEMARK OFFICE
CERTIFICATE OF CORRECTION

PATENT NO. : 10,555,919 B2
APPLICATION NO. : 15/525375
DATED : February 11, 2020
INVENTOR(S) : Mauricio Farez, Francisco J. Quintana and Jorge Correale Page 1 of 1

It is certified that error appears in the above-identified patent and that said Letters Patent is hereby corrected as shown below:

On the Title Page

In Column 1 (Item (71) Applicant), Line 1, delete "Hopsital," and insert -- Hospital, --

Signed and Sealed this
Ninth Day of June, 2020

Andrei Iancu
*Director of the United States Patent and Trademark Office*

SEQUENCE LISTING

<160> NUMBER OF SEQ ID NOS: 1

<210> SEQ ID NO 1
<211> LENGTH: 21
<212> TYPE: PRT
<213> ORGANISM: Artificial Sequence
<220> FEATURE:
<223> OTHER INFORMATION: MOG35-55 antigenic peptide

<400> SEQUENCE: 1

```
Met Glu Val Gly Trp Tyr Arg Ser Pro Phe Ser Arg Val Val His Leu
1               5                   10                  15

Tyr Arg Asn Gly Lys
            20
```